(12) United States Patent
Hu et al.

(10) Patent No.: US 10,036,029 B2
(45) Date of Patent: Jul. 31, 2018

(54) **MOLECULAR MARKERS FOR LOW PALMITIC ACID CONTENT IN SUNFLOWER (*HELIANTHUS ANNUS*), AND METHODS OF USING THE SAME**

(71) Applicant: Dow AgroSciences LLC, Indianapolis, IN (US)

(72) Inventors: Xueyi Hu, Westfield, IN (US); Mandy Sullivan-Gilbert, Lebanon, IN (US); Jan E. Backlund, Indianapolis, IN (US); James T. Gerdes, London (CA)

(73) Assignee: Dow AgroSciences LLC, Indianapolis, IN (US)

( * ) Notice: Subject to any disclaimer, the term of this patent is extended or adjusted under 35 U.S.C. 154(b) by 517 days.

(21) Appl. No.: 13/837,877

(22) Filed: Mar. 15, 2013

(65) Prior Publication Data

US 2013/0254927 A1    Sep. 26, 2013

Related U.S. Application Data

(60) Provisional application No. 61/613,383, filed on Mar. 20, 2012.

(51) Int. Cl.
| | | |
|---|---|---|
| *C12N 15/82* | (2006.01) | |
| *C12Q 1/6895* | (2018.01) | |
| *A01H 1/02* | (2006.01) | |
| *A01H 1/04* | (2006.01) | |
| *A01H 5/10* | (2018.01) | |

(52) U.S. Cl.
CPC .......... *C12N 15/8247* (2013.01); *A01H 1/02* (2013.01); *A01H 1/04* (2013.01); *A01H 5/10* (2013.01); *C12Q 1/6895* (2013.01); *C12Q 2600/156* (2013.01)

(58) Field of Classification Search
None
See application file for complete search history.

(56) References Cited

U.S. PATENT DOCUMENTS

| 5,461,171 | A | 10/1995 | Heaton et al. |
|---|---|---|---|
| 2009/0169706 | A1 * | 7/2009 | Gerdes ............... A01H 5/10 426/601 |
| 2011/0055946 | A1 | 3/2011 | Gerdes et al. |
| 2011/0131689 | A1 | 6/2011 | Gerdes et al. |
| 2011/0145952 | A1 | 6/2011 | Gerdes et al. |
| 2011/0277173 | A1 | 11/2011 | Campbell et al. |

FOREIGN PATENT DOCUMENTS

| CN | 101945573 | 1/2011 | |
|---|---|---|---|
| CN | 101998824 | 3/2011 | |
| WO | WO 2009102890 A2 * | 8/2009 | ............... A01H 5/10 |
| WO | WO-2009102890 A2 * | 8/2009 | ............... A01H 5/10 |

OTHER PUBLICATIONS

Qi et al (Chromosome location, DNA markers and rust resistance of the sunflower gene R5. Mol Breeding 30:745-756. Published online Nov. 2011).*
International Search Report and Written Opinion for International Application No. PCT/US2013/032217, dated Jun. 27, 2013.
Perez-Vich et al., "Stearoyl-ACP and oleoyl-PC desaturase genes cosegregate with quantitative trait loci underlying high stearic and high oleic acid mutant phenotypes in sunflower," Theoretical and Applied Genetics, (2002), vol. 104, No. 2-3, pp. 338-349.
Dehesh K et al : "Overexpression of a 3-ketoacyl-Acyl-Carrier Protein Synthase IIIs in Plants Reduces the Rate of Lipid Synthesis", Plant Physiology, Am erican Society of Plant Physiologists, Rockvi lle, MD, US, Feb. 1, 2001, vol. 125, pp. 1103-1114.
Gerdes et al.: "Identification and Characterization of Genes Conferring Reduced Saturate Oil in Sunflower (*Helianthus annuus* L.)", Feb. 29, 2012, Retrieved from the Internet.
Stoll et al : "Knockout of KasIII 1-16 regulation changes fatty acid composition in canola (*Brassica napus*)", European Journal of Li pid Science and Technology. , Apr. 1, 2006, vol. 108, No. 4, pp. 277-286.
Tang S et al : "Simple sequence repeat map 1-16 of the sunflower genome", Theoretical and Appli ed Genetics ; Internati onal Journal of Plant Breed ing Research, Springer, Berlin, DE, Dec. 1, 2002, vol. 105, No. 8, pp. 1124-1136.
Yu et al.: "Towards a saturated molecular genetic linkage map for cultivated sunflower", Crop Science : A Journal Serving the International Community of Crop Scientists, Crop Science Soci ety of America, US, Jan. 1, 2006, vol. 43, No . 1, pp. 367-387.

* cited by examiner

*Primary Examiner* — Medina A Ibrahim
*Assistant Examiner* — Wayne Zhong
(74) *Attorney, Agent, or Firm* — Marcia I. Rosenfeld; Magleby Cataxinos & Greenwood

(57) ABSTRACT

This disclosure concerns methods and compositions for identifying sunflower plants that have a low palmitic acid content phenotype. Some embodiments concern molecular markers to identify, select, and/or construct low palmitic acid content plants and germplasm, or to identify and counter-select relatively high palmitic acid content plants. This disclosure also concerns sunflower plants comprising a low palmitic acid content phenotype that are generated by methods utilizing at least one marker described herein.

9 Claims, 5 Drawing Sheets

SEQUENCE LISTING

<160> NUMBER OF SEQ ID NOS: 52

<210> SEQ ID NO 1
<211> LENGTH: 22
<212> TYPE: DNA
<213> ORGANISM: Artificial
<220> FEATURE:
<223> OTHER INFORMATION: Forward primer- marker HA0357_H757B

<400> SEQUENCE: 1
gttcctgtcg ggtaactgta gc                                            22

<210> SEQ ID NO 2
<211> LENGTH: 19

-continued

```
<212> TYPE: DNA
<213> ORGANISM: Artificial
<220> FEATURE:
<223> OTHER INFORMATION: Reverse primer- marker HA0357_H757B

<400> SEQUENCE: 2
cattgatgga gatggctgg                                           19

<210> SEQ ID NO 3
<211> LENGTH: 20
<212> TYPE: DNA
<213> ORGANISM: Artificial
<220> FEATURE:
<223> OTHER INFORMATION: Forward primer- marker HA0694B_H280R

<400> SEQUENCE: 3
gccgtgaata atgggattga                                          20

<210> SEQ ID NO 4
<211> LENGTH: 20
<212> TYPE: DNA
<213> ORGANISM: Artificial
<220> FEATURE:
<223> OTHER INFORMATION: Reverse primer- marker HA0694B_H280R

<400> SEQUENCE: 4
gattgggtca gcttgtgtga                                          20

<210> SEQ ID NO 5
<211> LENGTH: 23
<212> TYPE: DNA
<213> ORGANISM: Artificial
<220> FEATURE:
<223> OTHER INFORMATION: Forward primer- marker HA1485

<400> SEQUENCE: 5
gggaagtggg cttgtctatg tat                                      23

<210> SEQ ID NO 6
<211> LENGTH: 23
<212> TYPE: DNA
<213> ORGANISM: Artificial
<220> FEATURE:
<223> OTHER INFORMATION: Reverse primer- marker HA1485

<400> SEQUENCE: 6
aacacaccga aatcacctat gaa                                      23

<210> SEQ ID NO 7
<211> LENGTH: 22
<212> TYPE: DNA
<213> ORGANISM: Artificial
<220> FEATURE:
<223> OTHER INFORMATION: Forward primer- marker HA1838

<400> SEQUENCE: 7
agaggaatga gatcgggttg at                                       22

<210> SEQ ID NO 8
<211> LENGTH: 21
<212> TYPE: DNA
<213> ORGANISM: Artificial
<220> FEATURE:
<223> OTHER INFORMATION: Reverse primer- marker HA1838

<400> SEQUENCE: 8
```

```
gtgggacaac tcagcaacgt c                                              21

<210> SEQ ID NO 9
<211> LENGTH: 23
<212> TYPE: DNA
<213> ORGANISM: Artificial
<220> FEATURE:
<223> OTHER INFORMATION: Forward primer- marker HA1489_H280R

<400> SEQUENCE: 9
cttattccaa ggacgcatag tcg                                            23

<210> SEQ ID NO 10
<211> LENGTH: 23
<212> TYPE: DNA
<213> ORGANISM: Artificial
<220> FEATURE:
<223> OTHER INFORMATION: Reverse primer- marker HA1489_H280R

<400> SEQUENCE: 10
cgatggtatg attctcgacg tta                                            23

<210> SEQ ID NO 11
<211> LENGTH: 20
<212> TYPE: DNA
<213> ORGANISM: Artificial
<220> FEATURE:
<223> OTHER INFORMATION: Forward primer- marker HA1146B

<400> SEQUENCE: 11
acaccaacca gacgcagaat                                                20

<210> SEQ ID NO 12
<211> LENGTH: 20
<212> TYPE: DNA
<213> ORGANISM: Artificial
<220> FEATURE:
<223> OTHER INFORMATION: Reverse primer- marker HA1146B

<400> SEQUENCE: 12
gtgcaagaac gaggaagagg                                                20

<210> SEQ ID NO 13
<211> LENGTH: 24
<212> TYPE: DNA
<213> ORGANISM: Artificial
<220> FEATURE:
<223> OTHER INFORMATION: Forward primer- marker HA0037

<400> SEQUENCE: 13
gaacatggcc ataactcata gacg                                           24

<210> SEQ ID NO 14
<211> LENGTH: 16
<212> TYPE: DNA
<213> ORGANISM: Artificial
<220> FEATURE:
<223> OTHER INFORMATION: Reverse primer- marker HA0037

<400> SEQUENCE: 14
ccttcgaccc aacatc                                                    16

<210> SEQ ID NO 15
<211> LENGTH: 21
<212> TYPE: DNA
<213> ORGANISM: Artificial
```

```
<220> FEATURE:
<223> OTHER INFORMATION: Forward primer- marker HA0654

<400> SEQUENCE: 15
acgcacatga gagagaaaga g                                              21

<210> SEQ ID NO 16
<211> LENGTH: 20
<212> TYPE: DNA
<213> ORGANISM: Artificial
<220> FEATURE:
<223> OTHER INFORMATION: Reverse primer- marker HA0654

<400> SEQUENCE: 16
accttcgacc caacatcaag                                                20

<210> SEQ ID NO 17
<211> LENGTH: 23
<212> TYPE: DNA
<213> ORGANISM: Artificial
<220> FEATURE:
<223> OTHER INFORMATION: Forward primer- marker HA1620_H280R

<400> SEQUENCE: 17
tttcgtgatg gtgattgatg att                                            23

<210> SEQ ID NO 18
<211> LENGTH: 23
<212> TYPE: DNA
<213> ORGANISM: Artificial
<220> FEATURE:
<223> OTHER INFORMATION: Reverse primer- marker HA1620_H280R

<400> SEQUENCE: 18
cagcaactct gaccgtttca tta                                            23

<210> SEQ ID NO 19
<211> LENGTH: 21
<212> TYPE: DNA
<213> ORGANISM: Artificial
<220> FEATURE:
<223> OTHER INFORMATION: Forward primer- marker HA0031B

<400> SEQUENCE: 19
ctcacgaaac tcttcatgct g                                              21

<210> SEQ ID NO 20
<211> LENGTH: 18
<212> TYPE: DNA
<213> ORGANISM: Artificial
<220> FEATURE:
<223> OTHER INFORMATION: Reverse primer- marker HA0031B

<400> SEQUENCE: 20
ctctcacact tactgaac                                                  18

<210> SEQ ID NO 21
<211> LENGTH: 20
<212> TYPE: DNA
<213> ORGANISM: Artificial
<220> FEATURE:
<223> OTHER INFORMATION: Forward primer- marker HA0908

<400> SEQUENCE: 21
ttgtcttcat ctgcgtgtga                                                20
```

<210> SEQ ID NO 22
<211> LENGTH: 20
<212> TYPE: DNA
<213> ORGANISM: Artificial
<220> FEATURE:
<223> OTHER INFORMATION: Reverse primer- marker HA0908

<400> SEQUENCE: 22
ttgctgttgt tgatcggtgt                                               20

<210> SEQ ID NO 23
<211> LENGTH: 23
<212> TYPE: DNA
<213> ORGANISM: Artificial
<220> FEATURE:
<223> OTHER INFORMATION: Forward primer- marker HA1665

<400> SEQUENCE: 23
cctaagggga tgaattctct ttc                                           23

<210> SEQ ID NO 24
<211> LENGTH: 23
<212> TYPE: DNA
<213> ORGANISM: Artificial
<220> FEATURE:
<223> OTHER INFORMATION: Reverse primer- marker HA1665

<400> SEQUENCE: 24
aacttccaat gttctccaac cat                                           23

<210> SEQ ID NO 25
<211> LENGTH: 20
<212> TYPE: DNA
<213> ORGANISM: Artificial
<220> FEATURE:
<223> OTHER INFORMATION: Forward primer- marker HA0304A_H757B

<400> SEQUENCE: 25
gtgccctaac actgttccgt                                               20

<210> SEQ ID NO 26
<211> LENGTH: 19
<212> TYPE: DNA
<213> ORGANISM: Artificial
<220> FEATURE:
<223> OTHER INFORMATION: Reverse primer- marker HA0304A_H757B

<400> SEQUENCE: 26
agcgaaagga tcgagaatc                                                19

<210> SEQ ID NO 27
<211> LENGTH: 21
<212> TYPE: DNA
<213> ORGANISM: Artificial
<220> FEATURE:
<223> OTHER INFORMATION: Forward primer- marker HA0850_H757B

<400> SEQUENCE: 27
ccctggagtg tatgtccgtt a                                             21

<210> SEQ ID NO 28
<211> LENGTH: 20
<212> TYPE: DNA
<213> ORGANISM: Artificial
<220> FEATURE:
<223> OTHER INFORMATION: Reverse primer- marker HA0850_H757B -continued

<400> SEQUENCE: 28
atccgtctgc tgcctaatcc                                                20

<210> SEQ ID NO 29
<211> LENGTH: 20
<212> TYPE: DNA
<213> ORGANISM: Artificial
<220> FEATURE:
<223> OTHER INFORMATION: Forward primer- marker HA0743_H757B

<400> SEQUENCE: 29
acggaaagct cttgaaagca                                                20

<210> SEQ ID NO 30
<211> LENGTH: 20
<212> TYPE: DNA
<213> ORGANISM: Artificial
<220> FEATURE:
<223> OTHER INFORMATION: Reverse primer- marker HA0743_H757B

<400> SEQUENCE: 30
gcgggcattc caactagtaa                                                20

<210> SEQ ID NO 31
<211> LENGTH: 20
<212> TYPE: DNA
<213> ORGANISM: Artificial
<220> FEATURE:
<223> OTHER INFORMATION: Forward primer- marker HA0870

<400> SEQUENCE: 31
gtgcgttggc tcttatggat                                                20

<210> SEQ ID NO 32
<211> LENGTH: 20
<212> TYPE: DNA
<213> ORGANISM: Artificial
<220> FEATURE:
<223> OTHER INFORMATION: Reverse primer- marker HA0870

<400> SEQUENCE: 32
agtgatggca ttcccaattt                                                20

<210> SEQ ID NO 33
<211> LENGTH: 20
<212> TYPE: DNA
<213> ORGANISM: Artificial
<220> FEATURE:
<223> OTHER INFORMATION: Forward primer- marker HA0907

<400> SEQUENCE: 33
catgaacatc gccaattcag                                                20

<210> SEQ ID NO 34
<211> LENGTH: 20
<212> TYPE: DNA
<213> ORGANISM: Artificial
<220> FEATURE:
<223> OTHER INFORMATION: Reverse primer- marker HA0907

<400> SEQUENCE: 34
tgcaaggaac catcagaatc                                                20

<210> SEQ ID NO 35

<210> SEQ ID NO 35
<211> LENGTH: 19
<212> TYPE: DNA
<213> ORGANISM: Artificial
<220> FEATURE:
<223> OTHER INFORMATION: Forward primer- marker HA0612A_H757B

<400> SEQUENCE: 35
cttgggttct tcataactc                                             19

<210> SEQ ID NO 36
<211> LENGTH: 19
<212> TYPE: DNA
<213> ORGANISM: Artificial
<220> FEATURE:
<223> OTHER INFORMATION: Reverse primer- marker HA0612A_H757B

<400> SEQUENCE: 36
catgtaatca cctttcaag                                             19

<210> SEQ ID NO 37
<211> LENGTH: 22
<212> TYPE: DNA
<213> ORGANISM: Artificial
<220> FEATURE:
<223> OTHER INFORMATION: Forward primer- marker HA1923

<400> SEQUENCE: 37
aaccaaagat tcaaggcaat ca                                         22

<210> SEQ ID NO 38
<211> LENGTH: 21
<212> TYPE: DNA
<213> ORGANISM: Artificial
<220> FEATURE:
<223> OTHER INFORMATION: Reverse primer- marker HA1923

<400> SEQUENCE: 38
cagacattag acgcgaagca g                                          21

<210> SEQ ID NO 39
<211> LENGTH: 24
<212> TYPE: DNA
<213> ORGANISM: Artificial
<220> FEATURE:
<223> OTHER INFORMATION: Forward primer- markers HA1357A and
      HA1357B_H757B

<400> SEQUENCE: 39
cacaaaacaa tcgctaaaag aaca                                       24

<210> SEQ ID NO 40
<211> LENGTH: 23
<212> TYPE: DNA
<213> ORGANISM: Artificial
<220> FEATURE:
<223> OTHER INFORMATION: Reverse primer- markers HA1357A and
      HA1357B_H757B

<400> SEQUENCE: 40
aatgatgatg gtcacgaaga aga                                        23

<210> SEQ ID NO 41
<211> LENGTH: 21
<212> TYPE: DNA
<213> ORGANISM: Artificial
<220> FEATURE:
<223> OTHER INFORMATION: Forward primer- marker HA1819_H280R

<400> SEQUENCE: 41 gtttcggtg ggggattacg g                                          21

<210> SEQ ID NO 42
<211> LENGTH: 22
<212> TYPE: DNA
<213> ORGANISM: Artificial
<220> FEATURE:
<223> OTHER INFORMATION: Reverse primer- marker HA1819_H280R

<400> SEQUENCE: 42
atggtcgaca acaagcgcaa ac                                        22

<210> SEQ ID NO 43
<211> LENGTH: 20
<212> TYPE: DNA
<213> ORGANISM: Artificial
<220> FEATURE:
<223> OTHER INFORMATION: Forward primer- marker HA0894

<400> SEQUENCE: 43
tggtggaggt cactattgga                                           20

<210> SEQ ID NO 44
<211> LENGTH: 20
<212> TYPE: DNA
<213> ORGANISM: Artificial
<220> FEATURE:
<223> OTHER INFORMATION: Reverse primer- marker HA0894

<400> SEQUENCE: 44
aggaaagaag gaagccgaga                                           20

<210> SEQ ID NO 45
<211> LENGTH: 21
<212> TYPE: DNA
<213> ORGANISM: Artificial
<220> FEATURE:
<223> OTHER INFORMATION: Forward primer- marker HA1790

<400> SEQUENCE: 45
tccccaaact tgcgtgtagg t                                         21

<210> SEQ ID NO 46
<211> LENGTH: 23
<212> TYPE: DNA
<213> ORGANISM: Artificial
<220> FEATURE:
<223> OTHER INFORMATION: Reverse primer- marker HA1790

<400> SEQUENCE: 46
cattacaaac cacagctcct tcc                                       23

<210> SEQ ID NO 47
<211> LENGTH: 19
<212> TYPE: DNA
<213> ORGANISM: Artificial
<220> FEATURE:
<223> OTHER INFORMATION: Forward primer- marker HA0041

<400> SEQUENCE: 47
ctagcaacca acctcattg                                            19

<210> SEQ ID NO 48

```
<211> LENGTH: 20
<212> TYPE: DNA
<213> ORGANISM: Artificial
<220> FEATURE:
<223> OTHER INFORMATION: Reverse primer- marker HA0041

<400> SEQUENCE: 48
gtctccttct ctttctcggc                                              20

<210> SEQ ID NO 49
<211> LENGTH: 23
<212> TYPE: DNA
<213> ORGANISM: Artificial
<220> FEATURE:
<223> OTHER INFORMATION: Forward primer- marker HA1313

<400> SEQUENCE: 49
cgacccacct agtaaaagca aac                                          23

<210> SEQ ID NO 50
<211> LENGTH: 23
<212> TYPE: DNA
<213> ORGANISM: Artificial
<220> FEATURE:
<223> OTHER INFORMATION: Reverse primer- marker HA1313

<400> SEQUENCE: 50
tgccataaaa agatttggtc tcc                                          23

<210> SEQ ID NO 51
<211> LENGTH: 22
<212> TYPE: DNA
<213> ORGANISM: Artificial
<220> FEATURE:
<223> OTHER INFORMATION: Forward primer- marker HA1776_H757B

<400> SEQUENCE: 51
tcacaggaga atgcaaagag tg                                           22

<210> SEQ ID NO 52
<211> LENGTH: 25
<212> TYPE: DNA
<213> ORGANISM: Artificial
<220> FEATURE:
<223> OTHER INFORMATION: Reverse primer- marker HA1776_H757B

<400> SEQUENCE: 52
gcataatagg agtaactgcc aaaac                                        25
```

MOLECULAR MARKERS FOR LOW PALMITIC ACID CONTENT IN SUNFLOWER (*HELIANTHUS ANNUS*), AND METHODS OF USING THE SAME

CROSS-REFERENCE TO RELATED APPLICATION

This application claims the benefit of U.S. Provisional Patent Application Ser. No. 61/613,383, filed Mar. 20, 2012, the disclosure of which is hereby incorporated herein in its entirety by this reference.

TECHNICAL FIELD

The present disclosure relates to compositions and methods for identifying sunflower plants that have low palmitic acid content, where the methods use molecular genetic markers to identify, select and/or construct low palmitic acid content plants. The disclosure also relates to sunflower plants that display low palmitic acid content that are generated by the methods of the invention.

BACKGROUND

The cultivated sunflower (*Helianthus annuus* L.) is a major worldwide source of vegetable oil. In the United States, approximately 4 million acres of sunflower are planted annually, primarily in the Dakotas and Minnesota.

The very rapid expansion over the last decade of acreage planted in sunflower in the United States is due in part to several important developments in the field of sunflower breeding and varietal improvement, including the discovery of cytoplasmic male sterility and genes for fertility restoration. This discovery that allowed the production of hybrid sunflowers. The hybrids thus produced were introduced during the early 1970s. A description of cytoplasmic male sterility (CMS) and genetic fertility restoration in sunflowers is presented by Fick, "Breeding and Genetics," in *Sunflower Science and Technology* 279-338 (J. F. Carter ed. 1978), the contents of which are incorporated herein by reference.

Sunflower oil is comprised primarily of palmitic (16:0), stearic (18:0), oleic (18:1), linoleic (18:2) and linolenic (18:3) fatty acids. While other unusual fatty acids exist in plants, palmitic, stearic, oleic, linoleic, and linolenic acids comprise about 88% of the fatty acids present in the world production of vegetable oils. J. L. Harwood, "Plant Acyl Lipids: Structure, Distribution and Analysis," 4 *Lipids: Structure and Function*, P. K. Stumpf and E. E. Conn ed. (1988). Palmitic and stearic acids are saturated fatty acids that have been demonstrated in certain studies to contribute to an increase in the plasma cholesterol level, a factor contributing to the development of coronary heart disease. According to recent studies, vegetable oils high in unsaturated fatty acids (such as oleic and linoleic acid) may have the ability to lower plasma cholesterol.

Saturated fatty acids generally also have higher melting points than unsaturated fatty acids of the same carbon number, which contributes to cold tolerance problems in foodstuffs, and can further contribute to a waxy or greasy feel in the mouth of the foodstuff during ingestion. It is also known that food products made from fats and oils having less than about 3% saturated fatty acids will typically contain less than 0.5 grams saturated fat per serving, and as a result can be labeled as containing "zero saturated fat" under current labeling regulations.

There are numerous steps in the development of any novel, desirable plant germplasm. Plant breeding programs combine desirable traits from two or more cultivars or various broad-based sources into breeding pools, from which cultivars are developed by selfing and selection of desired phenotypes. The new cultivars are evaluated to determine which have commercial potential. Plant breeding begins with the analysis and definition of problems and weaknesses of the current germplasm, the establishment of program goals, and the definition of specific breeding objectives. The next step is selection of germplasm that possess the traits to meet the program goals. The goal is to combine in a single variety an improved combination of desirable traits from the parental germplasm. These important traits may include higher seed yield, resistance to diseases and insects, better stems and roots, tolerance to drought and heat, and better agronomic quality.

Choice of breeding or selection methods depends on the mode of plant reproduction, the heritability of the trait(s) being improved, and the type of cultivar used commercially (e.g., $F_1$ hybrid cultivar, pureline cultivar, etc.). For highly heritable traits, a choice of superior individual plants evaluated at a single location may be effective, whereas for traits with low heritability, selection should be based on mean values obtained from replicated evaluations of families of related plants. Popular selection methods commonly include pedigree selection, modified pedigree selection, mass selection, and recurrent selection.

The complexity of inheritance influences the choice of the breeding method. Backcross breeding is used to transfer one or a few favorable genes for a highly heritable trait into a desirable cultivar. This approach has been used extensively for breeding disease-resistant cultivars. Various recurrent selection techniques are used to improve quantitatively inherited traits controlled by numerous genes. The use of recurrent selection in self-pollinating crops depends on the ease of pollination, the frequency of successful hybrids from each pollination, and the number of hybrid offspring from each successful cross.

Each breeding program should include a periodic, objective evaluation of the efficiency of the breeding procedure. Evaluation criteria vary depending on the goal and objectives, but should include gain from selection per year (based on comparisons to an appropriate standard), overall value of the advanced breeding lines, and the number of successful cultivars produced per unit of input (e.g., per year, per dollar expended, etc.). Promising advanced breeding lines are then thoroughly tested and compared to appropriate standards in environments representative of the commercial target area(s) for three or more years. Candidates for new commercial cultivars are selected from among the best lines; those still deficient in a few traits may be used as parents to produce new populations for further selection. These processes, which lead to the final step of marketing and distribution, usually take from 8 to 12 years from the time the first cross is made. Therefore, development of new cultivars is a time-consuming process that requires precise forward planning, efficient use of resources, and a minimum of changes in direction.

A most difficult task in plant breeding is the identification of individuals that are genetically superior. One method of identifying a superior plant is to observe its performance relative to other experimental plants and to a widely grown standard cultivar. If a single observation is inconclusive, replicated observations provide a better estimate of its genetic worth. This task is so difficult, because (for most traits) the true genotypic value is masked by other confounding plant traits or environmental factors.

The goal of sunflower plant breeding is to develop new, unique, and superior sunflower cultivars and hybrids. The breeder initially selects and crosses two or more parental lines, followed by repeated selfing and selection, producing many new genetic combinations. The breeder can theoretically generate billions of different genetic combinations via crossing, selfing, and mutagenesis. Such a breeder has no direct control of the process at the cellular level. Therefore, two breeders will never develop the same line, or even very similar lines, having the same sunflower traits.

Each year, the plant breeder selects the germplasm to advance to the next generation. This germplasm is grown under unique and different geographical, climatic, and soil conditions. Further selections are then made, during and at the end of the growing season. The cultivars that are developed are unpredictable. This unpredictability is due to the breeder's selection, which occurs in unique environments, and which allows no control at the DNA level (using conventional breeding procedures), with millions of different possible genetic combinations being generated. A breeder of ordinary skill in the art cannot predict the final resulting lines he develops, except possibly in a very gross and general fashion. Similarly, the same breeder cannot produce the same cultivar twice by using the exact same original parents and the same selection techniques. This unpredictability results in the expenditure of large amounts of resources, monetary and otherwise, to develop superior new sunflower cultivars.

The development of new sunflower cultivars requires the development and selection of sunflower varieties, crossing of these varieties, and selection of superior hybrid crosses. Hybrid seed is produced by manual crosses between selected male-fertile parents, or by using male sterility systems. These hybrids are selected for certain single gene traits (e.g., pod color, flower color, pubescence color, and herbicide resistance) that indicate that the seed is truly a hybrid. Data on parental lines, as well as the phenotype of the hybrid, influence the breeder's decision regarding whether to continue with the specific hybrid cross.

Pedigree breeding is used commonly for the improvement of self-pollinating crops. In pedigree breeding, two parents that possess favorable, complementary traits are crossed to produce $F_1$ progeny. An $F_2$ population is produced by selfing one or several plants from the $F_1$ progeny generation. Selection of the best individuals may begin in the $F_2$ population; then, beginning in the $F_3$, the best individuals in the best families are selected. To improve the effectiveness of selection for traits with low heritability, replicated testing of families can begin in the $F_4$ generation. At an advanced stage of inbreeding (e.g., $F_6$ or $F_7$), the best lines or mixtures of lines with similar phenotypes are tested for potential release as new cultivars. Mass and recurrent selections can be used to improve populations of either self- or cross-pollinating crops. A genetically variable population of heterozygous individuals may be either identified or created by intercrossing several different parents. The best plants may be selected based on individual superiority, outstanding progeny, or excellent combining ability. The selected plants are intercrossed to produce a new population, in which further cycles of selection may be continued.

Backcross breeding has been used to transfer genes for a simply and highly heritable trait into a desirable homozygous cultivar, or inbred line, which is the recurrent parent. The source of the trait to be transferred is the "donor parent." The resulting plant is expected to have the attributes of the recurrent parent (e.g., cultivar), and the desirable trait transferred from the donor parent. After the initial cross, individuals possessing the phenotype of the donor parent are selected, and repeatedly crossed (backcrossed) to the recurrent parent. The resulting plant is expected to have the attributes of the recurrent parent and the desirable trait transferred from the donor parent.

In sunflower breeding, the "single-seed descent procedure" refers to the planting of a segregating population, followed by harvesting a sample of one seed per resulting plant, and using the harvested one-seed sample to plant the next generation. When the population has been advanced from the $F_2$ generation to the desired level of inbreeding, the plants from which lines are derived will each trace to different $F_2$ individuals. The number of plants in a population declines each generation, due to failure of some seeds to germinate or some plants to produce at least one seed. As a result, not all of the $F_2$ plants originally sampled in the population will be represented by a progeny when generation advance is completed.

In a multiple-seed procedure, sunflower breeders commonly harvest seeds from each plant in a population and thresh them together to form a bulk. Part of the bulk is used to plant the next generation, and part is put in reserve. This procedure has been referred to as modified single-seed descent. The multiple-seed procedure has been used to save labor involved in the harvest. It is considerably faster to remove seeds with a machine, than to remove one seed from each by hand for the single-seed procedure. The multiple-seed procedure also makes it possible to plant the same number of seeds of a population for each generation of inbreeding. Enough seeds are harvested to compensate for the number of plants that did not germinate or produce seed.

Proper testing should detect any major faults and establish the level of superiority or improvement of a new cultivar over current cultivars. In addition to showing superior performance, there should be a demand for a new cultivar that is compatible with industry standards, or that creates a new market. The testing preceding release of a new cultivar should take into consideration research and development costs as well as technical superiority of the final cultivar. The introduction of a new cultivar can incur additional costs to the seed producer, the grower, the processor, and the consumer due to special required advertising and marketing, altered seed and commercial production practices, and new product utilization. For seed-propagated cultivars, it must be feasible to produce seed easily and economically.

It is the goal of the plant breeder to select plants and enrich the plant population for individuals that have desired traits, for example, decreased palmitic acid content, leading ultimately to increased agricultural productivity. Consistent with the foregoing, a continuing goal of sunflower breeders is to develop stable, high-yielding cultivars that are agronomically sound. Current goals include maximization of the amount of grain produced on the land used, and the supply of food for both animals and humans. To accomplish these goals, the sunflower breeder must select and develop sunflower plants that have traits that result in superior cultivars, and do so in the most cost-effective manner. Molecular markers may be used in the process of marker-assisted selection (MAS) to aid in the identification and selection of individuals or families of individuals that possess inherited attributes that are linked to the markers.

BRIEF SUMMARY OF THE DISCLOSURE

Molecular markers that are linked to low palmitic acid content may be used to facilitate marker-assisted selection for the low palmitic acid content trait in sunflower. Marker-assisted selection provides significant advantages with respect to time, cost, and labor, when compared to palmitic acid content phenotyping. Disclosed herein are particular markers identified to be within or near low palmitic acid content QTL regions in the sunflower genome that are polymorphic in parent genotypes and linked (e.g., tightly linked) to a low palmitic acid content phenotype. These markers, offer superior utility in marker-assisted selection of sunflower plants and cultivars having low palmitic acid content.

Described herein are methods of identifying a first sunflower plant that displays low palmitic acid content or germplasm comprised within such a sunflower plant. A first sunflower plant or germplasm that displays low palmitic acid content may in some examples be a plant or germplasm comprising a lower (i.e., decreased) palmitic acid content than is observed in a parental plant or germplasm of the first plant or germplasm. A first sunflower plant or germplasm that displays low palmitic acid content may in some examples be a plant or germplasm comprising a lower palmitic acid content than is observed in a particular conventional plant or germplasm of the same species (e.g., sunflower) as the first plant or germplasm. Some embodiments of such methods may comprise detecting in the first sunflower plant or germplasm at least one marker linked to low palmitic acid content, wherein the at least one marker is selected from the group consisting of: HA0031B; HA0908; HA1665; HA0304A; HA0850; HA0743; HA0870; HA0907; HA0612A; and markers linked (e.g., tightly linked) to any of HA0031B, HA0908, HA1665, HA0304A, HA0850, HA0743, HA0870, HA0907, and HA0612A.

Also described are methods of producing an sunflower plant or germplasm having low palmitic acid content. Some embodiments of such methods may comprise introgressing at least one marker linked to low palmitic acid content from a first sunflower plant or germplasm into a second sunflower plant or germplasm to produce a sunflower plant or germplasm that is likely to have low palmitic acid content. In such examples, the at least one marker may be selected from the group consisting of: HA0031B; HA0908; HA1665; HA0304A; HA0850; HA0743; HA0870; HA0907; HA0612A; and markers linked to any of HA0031B, HA0908, HA1665, HA0304A, HA0850, HA0743, HA0870, HA0907, and HA0612A. A sunflower plant or germplasm produced by the foregoing methods is also included in particular embodiments.

Some embodiments include methods for producing a transgenic sunflower plant. Examples of such methods may comprise introducing one or more exogenous nucleic acid molecule(s) into a target sunflower plant or progeny thereof, wherein at least one of the one or more exogenous nucleic acid molecule(s) comprises a sunflower genomic nucleotide sequence that is linked to at least one marker that is linked to low palmitic acid content, or wherein at least one of the one or more exogenous nucleic acid molecule(s) comprises a nucleotide sequence that is specifically hybridizable to a nucleotide sequence that is linked to at least one marker that is linked to low palmitic acid content. A marker that is linked to low palmitic acid content may be selected from the group consisting of: HA0031B; HA0908; HA1665; HA0304A; HA0850; HA0743; HA0870; HA0907; HA0612A; and markers linked to any of HA0031B, HA0908, HA1665, HA0304A, HA0743, HA0870, HA0907, and HA0612A. In certain examples the foregoing methods for producing a transgenic sunflower plant, a resulting transgenic sunflower plant may comprise low palmitic acid content.

Some embodiments include systems and kits for identifying a sunflower plant that is likely to comprise low palmitic acid content. Particular examples of such systems and kits may comprise a set of nucleic acid probes, each comprising a nucleotide sequence that is specifically hybridizable to a nucleotide sequence that is linked in sunflower to at least one marker that is linked to low palmitic acid content. A marker that is linked in sunflower to low palmitic acid content may be selected from the group consisting of: HA0031B; HA0908; HA1665; HA0304A; HA0850; HA0743; HA0870; HA0907; HA0612A; and markers linked to any of HA0031B, HA0908, HA1665, HA0304A, HA0850, HA0743, HA0870, HA0907, and HA0612A. Particular examples of systems and kits for identifying a sunflower plant that is likely to comprise low palmitic acid content may also comprise a detector that is configured to detect one or more signal outputs from the set of nucleic acid probes, or an amplicon thereof, thereby identifying the presence or absence of the at least one marker that is linked to low palmitic acid content. Specific examples include instructions that correlate the presence or absence of the at least one marker with the likely decrease in palmitic acid content.

DETAILED DESCRIPTION

I. Overview of Several Embodiments

Figure 1:
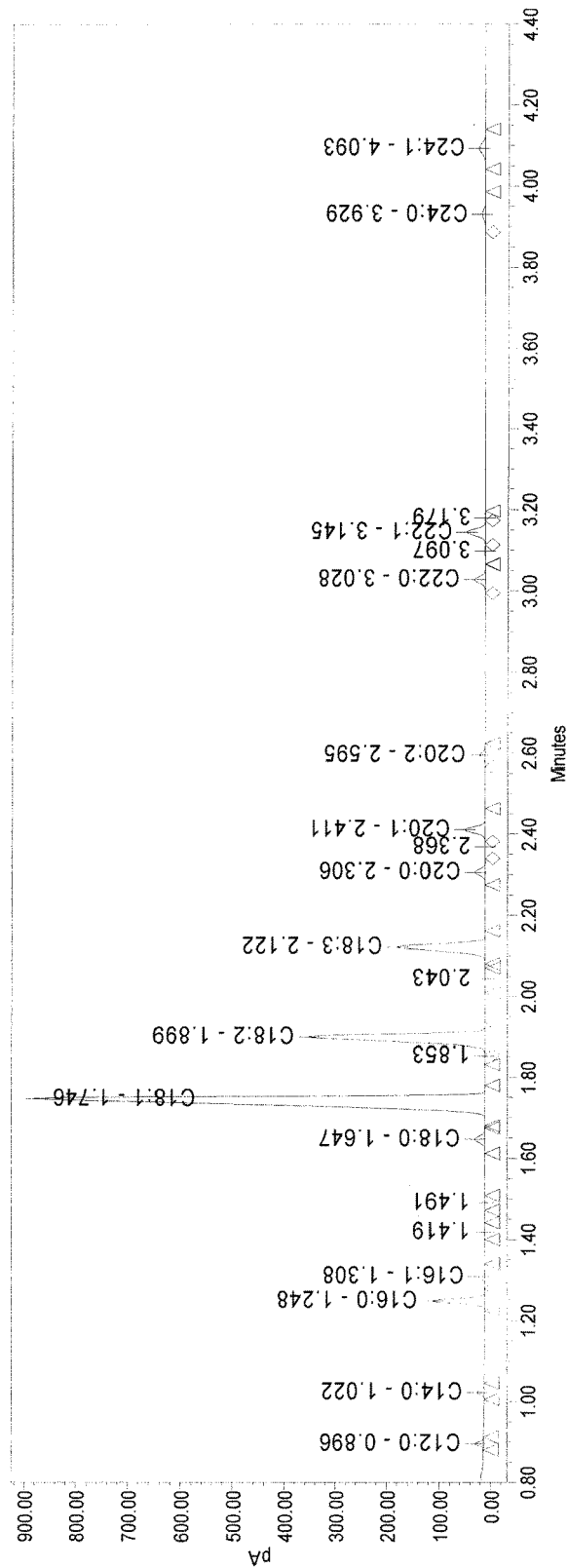
FIG. 1 includes a GC-FID FAME chromatogram showing the identification of palmitic acid methyl ester peaks by comparison with the retention times of methyl ester reference standards. Individual percent areas were calculated for all analytes in the reference standard based upon the total integrated peak areas. A heptane blank was also injected to identify any contamination on the GC.

It is desirable for a number of reasons to produce a sunflower oil having low levels of palmitic and stearic acids and high levels of oleic or linoleic acids. Embodiments of the invention include, for example, compositions and methods for identifying sunflower plants comprising a low palmitic acid content and/or germplasm carrying a genotype that is predictive and determinative of a low palmitic acid phenotype. Methods of making such sunflower plants and germplasm are included in some embodiments. Such methods may include, for example and without limitation, introgression of desired low palmitic acid content marker alleles and/or genetic transformation methods. Sunflower plants and/or germplasm made by the methods such as the foregoing are included in particular embodiments. Systems and kits for selecting sunflower plants comprising a low palmitic acid content and/or germplasm carrying a genotype that is predictive and determinative of a low palmitic acid phenotype are also a feature of certain embodiments.

The identification and selection of sunflower plants comprising a low palmitic acid content using MAS are capable of providing an effective and environmentally friendly approach for generating plants with desirable oil content. Embodiments of the present invention provide a number of sunflower marker loci and QTL chromosome intervals that demonstrate statistically significant co-segregation with (and therefore are predictive and determinative of) low palmitic acid content. Detection of these markers, or additional loci linked to the markers that are therefore equivalent thereto, may be used in marker-assisted sunflower breeding programs to produce low palmitic acid content plants and germplasm.

Some embodiments provide methods for identifying a first sunflower plant or germplasm (e.g., a line or variety) that displays low palmitic acid content. In some examples, at least one allele of one or more marker locus (e.g., a plurality of marker loci) that is linked (e.g., tightly linked) with a low palmitic acid trait is/are detected in the first sunflower plant or gemiplasm. The marker loci may be selected from the loci in FIG. 4, including: HA0031B, HA0908, HA1665, HA0304A, HA0850, HA0743, HA0870, HA0907, HA0612A, and other markers that are linked to at least one of the foregoing QTL markers.

In some examples, a plurality of maker loci may be selected or identified in the same plant or germplasm. All combinations of, for example, HA0031B, HA0908, HA1665, HA0304A, HA0850, HA0743, HA0870, HA0907, HA0612A, and other markers that are linked to at least one of the foregoing QTL markers, may be included in a plurality of marker loci to be selected or identified in a plant or germplasm.

In aspects of some embodiments, the palmitic acid content of a sunflower plant can be quantitated using any suitable means or method known in the art.

II. Abbreviations

AFLP amplified fragment length polymorphism
ASH allele specific hybridization
CCD charge coupling device
EST expressed sequence tag
FAME fatty acid methyl ester
FID flame ionization detector
GC gas chromatography
LCR ligase chain reaction
LG linkage group
LNA locked nucleic acid
LOD logarithm (base 10) of odds
MAS marker-assisted selection
NASBA nucleic acid sequence based amplification
NIR near infrared (spectroscopy)
NMR nuclear magnetic resonance (spectroscopy)
ORF open reading frame
PCR polymerase chain reaction
PNA peptide nucleic acid
QTL quantitative trait locus
RAPD randomly amplified polymorphic DNA
RFLP restriction fragment length polymorphism
RT-PCR reverse transcriptase-PCR
SNP single nucleotide polymorphism
SSCP single-strand conformation polymorphism
SSR simple sequence repeat III. Terms As used in this application, including the claims, terms in the singular and the singular forms, "a," "an," and "the," for example, include plural referents, unless the content clearly dictates otherwise. Thus, for example, a reference to "plant," "the plant," or "a plant" also refers to a plurality of plants. Furthermore, depending on the context, use of the term, "plant," may also refer to genetically similar or identical progeny of that plant. Similarly, the term, "nucleic acid," may refer to many copies of a nucleic acid molecule. Likewise, the term "probe" may refer to many similar or identical probe molecules.

Numeric ranges are inclusive of the numbers defining the range, and include each integer and non-integer fraction within the defined range. Unless defined otherwise, all technical and scientific terms used herein have the same meaning as commonly understood by one of ordinary skill in the art.

In order to facilitate review of the various embodiments described in this disclosure, the following explanation of specific terms is provided:

Isolated: An "isolated" biological component (such as a nucleic acid or protein) has been substantially separated, produced apart from, or purified away from other biological components in the cell of the organism in which the component naturally occurs (i.e., other chromosomal and extra-chromosomal DNA and RNA, and proteins), while effecting a chemical or functional change in the component (e.g., a nucleic acid may be isolated from a chromosome by breaking chemical bonds connecting the nucleic acid to the remaining DNA in the chromosome). Nucleic acid molecules and proteins that have been "isolated" include nucleic acid molecules and proteins purified by standard purification methods. The term also embraces nucleic acids and proteins prepared by recombinant expression in a host cell, as well as chemically synthesized nucleic acid molecules, proteins, and peptides.

Mapping population: As used herein, the term "mapping population" may refer to a plant population (e.g., a sunflower plant population) used for gene mapping. Mapping populations are typically obtained from controlled crosses of parent genotypes, as may be provided by two inbred lines. Decisions on the selection of parents, mating design for the development of a mapping population, and the type of markers used depend upon the gene to be mapped, the availability of markers, and the molecular map. The parents of plants within a mapping population should have sufficient variation for a trait(s) of interest at both the nucleic acid sequence and phenotype level. Variation of the parents' nucleic acid sequence is used to trace recombination events in the plants of the mapping population. The availability of informative polymorphic markers is dependent upon the amount of nucleic acid sequence variation. Thus, informative markers may not be identified in particular crosses of parent genotypes, though such markers may exist.

A "genetic map" is a description of genetic linkage relationships among loci on one or more chromosomes (or linkage groups) within a given species, as may be determined by analysis of a mapping population. In some examples, a genetic map may be depicted in a diagrammatic or tabular form. The term "genetic mapping" may refer to the process of defining the linkage relationships of loci through the use of genetic markers, mapping populations segregating for the markers, and standard genetic principles of recombination frequency. A "genetic map location" refers to a location on a genetic map (relative to surrounding genetic markers on the same linkage group or chromosome) where a particular marker can be found within a given species. In contrast, a "physical map of the genome" refers to absolute distances (for example, measured in base pairs or isolated and overlapping contiguous genetic fragments) between markers within a given species. A physical map of the genome does not necessarily reflect the actual recombination frequencies observed in a test cross of a species between different points on the physical map.

Cross: As used herein, the term "cross" or "crossed" refers to the fusion of gametes via pollination to produce progeny (e.g., cells, seeds, and plants). This term encompasses both sexual crosses (i.e., the pollination of one plant by another) and selfing (i.e., self-pollination, for example, using pollen and ovule from the same plant).

Backcrossing: Backcrossing methods may be used to introduce a nucleic acid sequence into plants. The backcrossing technique has been widely used for decades to introduce new traits into plants. N. Jensen, Ed. *Plant Breeding Methodology*, John Wiley & Sons, Inc., 1988. In a typical backcross protocol, the original variety of interest (recurrent parent) is crossed to a second variety (non-recurrent parent) that carries a gene of interest to be transferred. The resulting progeny from this cross are then crossed again to the recurrent parent, and the process is repeated until a plant is obtained wherein essentially all of the desired morphological and physiological characteristics of the recurrent plant are recovered in the converted plant, in addition to the transferred gene from the non-recurrent parent.

Introgression: As used herein, the term "introgression" refers to the transmission of an allele at a genetic locus into a genetic background. In some embodiments, introgression of a specific allele form at the locus may occur by transmitting the allele form to at least one progeny via a sexual cross between two parents of the same species, where at least one of the parents has the specific allele form in its genome. Progeny comprising the specific allele form may be repeatedly backcrossed to a line having a desired genetic background. Backcross progeny may be selected for the specific allele form, so as to produce a new variety wherein the specific allele form has been fixed in the genetic background. In some embodiments, introgression of a specific allele form may occur by recombination between two donor genomes (e.g., in a fused protoplast), where at least one of the donor genomes has the specific allele form in its genome. Introgression may involve transmission of a specific allele form that may be, for example and without limitation, a selected allele form of a marker allele; a QTL; and/or a transgene.

Germplasm: As used herein, the term "germplasm" refers to genetic material of or from an individual plant, a group of plants (e.g., a plant line, variety, and family), and a clone derived from a plant or group of plants. A germplasm may be part of an organism or cell, or it may be separate (e.g., isolated) from the organism or cell. In general, germplasm provides genetic material with a specific molecular makeup that is the basis for hereditary qualities of the plant. As used herein, "germplasm" refers to cells of a specific plant; seed; tissue of the specific plant (e.g., tissue from which new plants may be grown); and non-seed parts of the specific plant (e.g., leaf, stem, pollen, and cells).

As used herein, the term "germplasm" is synonymous with "genetic material," and it may be used to refer to seed (or other plant material) from which a plant may be propagated. A "germplasm bank" may refer to an organized collection of different seed or other genetic material (wherein each genotype is uniquely identified) from which a known cultivar may be cultivated, and from which a new cultivar may be generated. In embodiments, a germplasm utilized in a method or plant as described herein is from a sunflower line or variety. In particular examples, a germplasm is seed of the sunflower line or variety. In particular examples, a germplasm is a nucleic acid sample from the sunflower line or variety.

Gene: As used herein, the term "gene" (or "genetic element") may refer to a heritable genomic DNA sequence with functional significance. The term "gene" may also be used to refer to, for example and without limitation, a cDNA and/or an mRNA encoded by a heritable genomic DNA sequence.

Genotype: As used herein, the term "genotype" refers to the genetic constitution of an individual (or group of individuals) at one or more particular loci. The genotype of an individual or group of individuals is defined and described by the allele forms at the one or more loci that the individual has inherited from its parents. The term genotype may also be used to refer to an individual's genetic constitution at a single locus, at multiple loci, or at all the loci in its genome. A "haplotype" is the genotype of an individual at a plurality of genetic loci. In some examples, the genetic loci described by a haplotype may be physically and genetically linked; i.e., the loci may be positioned on the same chromosome segment.

Quantitative trait locus: Specific chromosomal loci (or intervals) may be mapped in an organism's genome that correlates with particular quantitative phenotypes. Such loci are termed quantitative trait loci, or QTL. As used herein, the term "quantitative trait locus" (QTL) may refer to stretches of DNA that have been identified as likely DNA sequences (e.g., genes, non-coding sequences, and/or intergenic sequences) that underlie a quantitative trait, or phenotype, that varies in degree, and can be attributed to the interactions between two or more DNA sequences (e.g., genes, non-coding sequences, and/or intergenic sequences) or their expression products and their environment. Thus, the term "quantitative trait locus" includes polymorphic genetic loci with at least two alleles that differentially affect the expression of a phenotypic trait in at least one genetic background (e.g., in at least one breeding population or progeny). In practice, QTLs can be molecularly identified to help map regions of the genome that contain sequences involved in specifying a quantitative trait, such as reduced palmitic acid content.

As used herein, the term "QTL interval" may refer to stretches of DNA that are linked to the genes that underlie the QTL trait. A QTL interval is typically, but not necessarily, larger than the QTL itself. A QTL interval may contain stretches of DNA that are 5' and/or 3' with respect to the QTL.

Multiple experimental paradigms have been developed to identify and analyze QTLs. See, e.g., Jansen (1996) *Trends Plant Sci.* 1:89. The majority of published reports on QTL mapping in crop species have been based on the use of a bi-parental cross (Lynch and Walsh (1997) *Genetics and Analysis of Quantitative Traits*, Sinauer Associates, Sunderland). Typically, these paradigms involve crossing one or more parental pairs that can be, for example, a single pair derived from two inbred strains, or multiple related or unrelated parents of different inbred strains or lines, which each exhibit different characteristics relative to the phenotypic trait of interest. Typically, this experimental protocol involves deriving 100 to 300 segregating progeny from a single cross of two divergent inbred lines that are, for example, selected to maximize phenotypic and molecular marker differences between the lines. The parents and segregating progeny are genotyped for multiple marker loci, and evaluated for one to several quantitative traits (e.g., disease resistance). QTLs are then identified as significant statistical associations between genotypic values and phenotypic variability among the segregating progeny. The strength of this experimental protocol comes from the utilization of the inbred cross, because the resulting $F_1$ parents all have the same linkage phase (how the alleles were joined in the parental generation). Thus, after selfing of $F_1$ plants, all segregating $F_2$ progeny are informative and linkage disequilibrium is maximized, the linkage phase is known, there are only two QTL alleles, and (except for backcross progeny) the frequency of each QTL allele is 0.5.

Numerous statistical methods for determining whether markers are genetically linked to a QTL (or to another marker) are known to those of skill in the art and include, for example and without limitation, standard linear models, such as ANOVA or regression mapping (Haley and Knott (1992) *Heredity* 69:315); and maximum likelihood methods, such as expectation-maximization algorithms (e.g., Lander and Botstein (1989) *Genetics* 121:185-99; Jansen (1992) *Theor. Appl. Genet.* 85:252-60; Jansen (1993) *Biometrics* 49:227-31; Jansen (1994) "Mapping of quantitative trait loci by using genetic markers: an overview of biometrical models," in J. W. van Ooijen and J. Jansen (eds.), *Biometrics in Plant breeding: applications of molecular markers*, pp. 116-24, CPRO-DLO Netherlands; Jansen (1996) *Genetics* 142:305-11; and Jansen and Stam (1994) *Genetics* 136:1447-55).

Exemplary statistical methods include single point marker analysis; interval mapping (Lander and Botstein (1989) *Genetics* 121:185); composite interval mapping; penalized regression analysis; complex pedigree analysis; MCMC analysis; MQM analysis (Jansen (1994) Genetics 138:871); HAPLO-IM+ analysis, HAPLO-MQM analysis, and HAPLO-MQM+ analysis; Bayesian MCMC; ridge regression; identity-by-descent analysis; and Haseman-Elston regression, any of which are suitable in the context of particular embodiments of the invention. Alternative statistical methods applicable to complex breeding populations that may be used to identify and localize QTLs in particular examples are described in U.S. Pat. No. 6,399,855 and PCT International Patent Publication No. WO0149104 A2. All of these approaches are computationally intensive and are usually performed with the assistance of a computer based system and specialized software. Appropriate statistical packages are available from a variety of public and commercial sources, and are known to those of skill in the art.

Marker: Although specific DNA sequences that encode proteins are generally well-conserved across a species, other regions of DNA (e.g., non-coding DNA and introns) tend to develop and accumulate polymorphism, and therefore, may be variable between individuals of the same species. The genomic variability can be of any origin, for example, the variability may be due to DNA insertions, deletions, duplications, repetitive DNA elements, point mutations, recombination events, and the presence and sequence of transposable elements. Such regions may contain useful molecular genetic markers. In general, any differentially inherited polymorphic trait (including nucleic acid polymorphisms) that segregates among progeny is a potential marker.

As used herein, the terms "marker" and "molecular marker" refer to a nucleotide sequence or encoded product thereof (e.g., a protein) used as a point of reference when identifying a linked locus. Thus, a marker may refer to a gene or nucleotide sequence that can be used to identify plants having a particular allele. A marker may be described as a variation at a given genomic locus. A genetic marker may be a short DNA sequence, such as a sequence surrounding a single base-pair change (single nucleotide polymorphism, or "SNP"), or a long one, for example, a microsatellite/simple sequence repeat ("SSR"). A "marker allele" or "marker allele form" refers to the version of the marker that is present in a particular individual. The term "marker" as used herein may refer to a cloned segment of chromosomal DNA, and may also or alternatively refer to a DNA molecule that is complementary to a cloned segment of chromosomal DNA. The term also refers to nucleic acid sequences complementary to genomic marker sequences, such as nucleic acid primers and probes.

A marker may be described, for example, as a specific polymorphic genetic element at a specific location in the genetic map of an organism. A genetic map may be a graphical representation of a genome (or a portion of a genome, such as a single chromosome) where the distances between landmarks on the chromosome are measured by the recombination frequencies between the landmarks. A genetic landmark can be any of a variety of known polymorphic markers, for example and without limitation: simple sequence repeat (SSR) markers; restriction fragment length polymorphism (RFLP) markers; and single nucleotide polymorphism (SNP) markers. As one example, SSR markers can be derived from genomic or expressed nucleic acids (e.g., expressed sequence tags (ESTs)).

Additional markers include, for example and without limitation, ESTs; amplified fragment length polymorphisms (AFLPs) (Vos et al. (1995) *Nucl. Acids Res.* 23:4407; Becker et al. (1995) *Mol. Gen. Genet.* 249:65; Meksem et al. (1995) *Mol. Gen. Genet.* 249:74); randomly amplified polymorphic DNA (RAPD), and isozyme markers. Isozyme markers may be employed as genetic markers, for example, to track isozyme markers or other types of markers that are linked to a particular first marker. Isozymes are multiple forms of enzymes that differ from one another with respect to amino acid sequence (and therefore with respect to their encoding nucleic acid sequences). Some isozymes are multimeric enzymes containing slightly different subunits. Other isozymes are either multimeric or monomeric, but have been cleaved from a pro-enzyme at different sites in the pro-enzyme amino acid sequence. Isozymes may be characterized and analyzed at the protein level or at the nucleic acid level. Thus, any of the nucleic acid based methods described herein can be used to analyze isozyme markers in particular examples.

"Genetic markers" include alleles that are polymorphic in a population, where the alleles of may be detected and distinguished by one or more analytic methods (e.g., RFLP analysis, AFLP analysis, isozyme marker analysis, SNP analysis, and SSR analysis). The term "genetic marker" may also refer to a genetic locus (a "marker locus") that may be used as a point of reference when identifying a genetically linked locus (e.g., QTL). Such a marker may also be referred to as a "QTL marker."

The nature of the foregoing physical landmarks (and the methods used to detect them) vary, but all of these markers are physically distinguishable from each other (as well as from the plurality of alleles of any one particular marker) on the basis of polynucleotide length and/or sequence. Numerous methods for detecting molecular markers and identifying marker alleles are well-established. A wide range of protocols are known to one of skill in the art for detecting this variability, and these protocols are frequently specific for the type of polymorphism they are designed to detect. Such protocols include, for example and without limitation, PCR amplification; detection of single-strand conformation polymorphism (SSCP), e.g., via electrophoresis; and self-sustained sequence replication (3 SR) (see Chan and Fox (1999) *Reviews in Medical Microbiology* 10:185-96).

The primary motivation for developing molecular marker technologies from the perspective of plant breeders has been to increase breeding efficiency through MAS. A molecular marker allele that demonstrates linkage disequilibrium with a desired phenotypic trait (e.g., a QTL) provides a useful tool for the selection of the desired trait in a plant population. The key components to the implementation of an MAS approach are the creation of a dense (information rich) genetic map of molecular markers in the plant germplasm; the detection of at least one QTL based on statistical associations between marker and phenotypic variability; the definition of a set of particular useful marker alleles based on the results of the QTL analysis; and the use and/or extrapolation of this information to the current set of breeding germplasm to enable marker-based selection decisions to be made.

Genetic variability, for example as determined in a mapping population, may be observed between different populations of the same species (e.g., sunflower). In spite of the variability in the genetic map that may occur between populations of the same species, genetic map and marker information derived from one population generally remains useful across multiple populations for the purposes of identification and/or selection of plants and/or germplasm comprising traits that are linked to the markers and counter-selection of plants and/or germplasm comprising undesirable traits.

Two types of markers used in particular MAS protocols described herein are SSR markers, and SNP markers. SSR markers include any type of molecular heterogeneity that results in nucleic acid sequence length variability. Exemplary SSR markers are short (up to several hundred base pairs) segments of DNA that consist of multiple tandem repeats of a two or three base-pair sequence. These repeated sequences result in highly polymorphic DNA regions of variable length due to poor replication fidelity (e.g., by polymerase slippage). SSRs appear to be randomly dispersed through the genome, and are generally flanked by conserved regions. SSR markers may also be derived from RNA sequences (in the form of a cDNA, a partial cDNA, or an EST), as well as genomic material.

The heterogeneity of SSR markers make them well-suited for use as molecular genetic markers. For example, SSR genomic variability is inherited, and it is multi-allelic, co-dominant, and reproducibly detectable. The proliferation of increasingly sophisticated amplification-based detection techniques (e.g., PCR-based techniques) provides a variety of sensitive methods for the detection of nucleotide sequence heterogeneity between samples. Probes (e.g., nucleic acid primers) may be designed to hybridize to conserved regions that flank the SSR, and the probes may be used to amplify the variable SSR region. The differently sized amplicons generated from an SSR region have characteristic and reproducible sizes. Differently sized SSR amplicons observed from two homologous chromosomes from an individual, or from different individuals, in the plant population define SSR marker alleles. As long as there exist at least two SSR marker alleles that produce PCR products with different sizes, the SSR may be employed as a marker.

Linkage (dis)equilibrium: As used herein, the term "linkage equilibrium" refers to the situation where two markers independently segregate; i.e., the markers sort randomly among progeny. Markers that show linkage equilibrium are considered unlinked (whether or not they lie on the same chromosome). As used herein, the term "linkage disequilibrium" refers to the situation where two markers segregate in a non-random manner; i.e., the markers have a recombination frequency of less than 50% (and thus by definition, are separated by less than 50 cM on the same linkage group). In some examples, markers that show linkage disequilibrium are considered linked.

Linked, tightly linked, and extremely tightly linked: As used herein, linkage between genes or markers may refer to the phenomenon in which genes or markers on a chromosome show a measurable probability of being passed on together to individuals in the next generation. Thus, linkage of one marker to another marker or gene may be measured and/or expressed as a recombination frequency. The closer two genes or markers are to each other, the closer to "1" this probability becomes. Thus, the term "linked" may refer to one or more genes or markers that are passed together with a gene with a probability greater than 0.5 (which is expected from independent assortment where markers/genes are located on different chromosomes). When the presence of a gene contributes to a phenotype in an individual, markers that are linked to the gene may be said to be linked to the phenotype. Thus, the term "linked" may refer to a relationship between a marker and a gene, or between a marker and a phenotype.

A relative genetic distance (determined by crossing over frequencies and measured in centimorgans (cM)) is generally proportional to the physical distance (measured in base pairs) that two linked markers or genes are separated from each other on a chromosome. One centimorgan is defined as the distance between two genetic markers that show a 1% recombination frequency (i.e., a crossing-over event occurs between the two markers once in every 100 cell divisions). In general, the closer one marker is to another marker or gene (whether the distance between them is measured in terms of genetic distance or physical distance), the more tightly they are linked. Because chromosomal distance is approximately proportional to the frequency of recombination events between traits, there is an approximate physical distance that correlates with recombination frequency. For example, in sunflower, 1 cM correlates, on average, to about 400 kb.

Thus, the term "linked" may refer herein to one or more genes or markers that are physically located within about 4.0 Mb of one another on the same sunflower chromosome (i.e., about 10 cM). Thus, two "linked" genes or markers may be separated by 4.1 Mb; about 4.0 Mb; about 3.0 Mb; about 2.5 Mb; 2.1 Mb; 2.00 Mb; about 1.95 Mb; about 1.90 Mb; about 1.85 Mb; about 1.80 Mb; about 1.75 Mb; about 1.70 Mb; about 1.65 Mb; about 1.60 Mb; about 1.55 Mb; about 1.50 Mb; about 1.45 Mb; about 1.40 Mb; about 1.35 Mb; about 1.30 Mb; about 1.25 Mb; about 1.20 Mb; about 1.15 Mb;

about 1.10 Mb; about 1.05 Mb; about 1.00 Mb; about 0.95 Mb; about 0.90 Mb; about 0.85 Mb; about 0.80 Mb; about 0.75 Mb; about 0.70 Mb; about 0.65 Mb; about 0.60 Mb; about 0.55 Mb; about 0.50 Mb; about 0.45 Mb; about 0.40 Mb; about 0.35 Mb; about 0.30 Mb; about 0.25 Mb; about 0.20 Mb; about 0.15 Mb; about 0.10 Mb; about 0.05 Mb; about 0.025 Mb; and about 0.01 Mb.

As used herein, the term "tightly linked" may refer to one or more genes or markers that are located within about 2.0 Mb of one another on the same chromosome. Thus, two "tightly linked" genes or markers may be separated by 2.1 Mb; about 1.75 Mb; about 1.5 Mb; about 1.0 Mb; about 0.9 Mb; about 0.8 Mb; about 0.7 Mb; about 0.6 Mb; about 0.55 Mb; 0.5 Mb; about 0.45 Mb; about 0.4 Mb; about 0.35 Mb; about 0.3 Mb; about 0.25 Mb; about 0.2 Mb; about 0.15 Mb; about 0.1 Mb; and about 0.05 Mb.

As used herein, the term "extremely tightly linked" may refer to one or more genes or markers that are located within about 500 kb of one another on the same chromosome. Thus, two "extremely tightly linked" genes or markers may be separated by 600 kb; about 450 kb; about 400 kb; about 350 kb; about 300 kb; about 250 kb; about 200 kb; about 175 kb; about 150 kb; about 125 kb; about 120 kb; about 115 kb; about 110 kb; about 105 kb; 100 kb; about 95 kb; about 90 kb; about 85 kb; about 80 kb; about 75 kb; about 70 kb; about 65 kb; about 60 kb; about 55 kb; about 50 kb; about 45 kb; about 40 kb; about 35 kb; about 30 kb; about 25 kb; about 20 kb; about 15 kb; about 10 kb; about 5 kb; and about 1 kb.

The closer a particular marker is to a gene that encodes a polypeptide that contributes to a particular phenotype (whether measured in terms of genetic or physical distance), the more tightly linked is the particular marker to the phenotype. In view of the foregoing, it will be appreciated that markers linked to a particular gene or phenotype include those markers that are tightly linked, and those markers that are extremely tightly linked, to the gene or phenotype. In some embodiments, the closer a particular marker is to a gene that encodes a polypeptide that contributes to a low palmitic acid content phenotype (whether measured in terms of genetic or physical distance), the more tightly linked is the particular marker to the low palmitic acid content phenotype. Thus, linked, tightly linked, and extremely tightly genetic markers of a low palmitic acid content phenotype in sunflower may be useful in MAS programs to identify sunflower varieties comprising a decreased palmitic acid content (when compared to parental varieties and/or at least one particular conventional variety), to identify individual sunflower plants comprising a decreased palmitic acid content, and to breed this trait into other sunflower varieties to decrease palmitic acid content.

In some embodiments, the linkage relationship between a molecular marker and a phenotype may be expressed as a "probability" or "adjusted probability." Within this context, a probability value is the statistical likelihood that a particular combination of a phenotype and the presence or absence of a particular marker allele form is random. Thus, the lower the probability score, the greater the likelihood that the phenotype and the particular marker allele form will co-segregate. In some examples, the probability score may be described as "significant" or "non-significant." In particular examples, a probability score of 0.05 (p=0.05 (a 5% probability)) of random assortment is considered a "significant" indication of co-segregation. However, a significant probability may in other examples be any probability of less than 50% (p=0.5). For instance, a significant probability may be less than 0.25; less than 0.20; less than 0.15; or less than 0.1.

Figure 4:
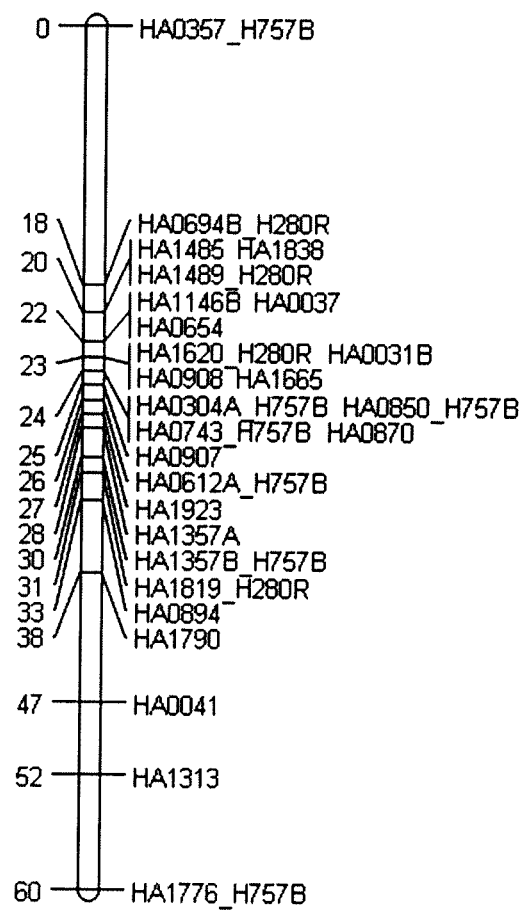
FIG. 4 includes a schematic representation of a major locus on linkage group 5 (LG5) for low palmitic acid content in sunflower. Several SSR markers have been identified to be tightly linked or flanking the locus as depicted.
Figure 5:
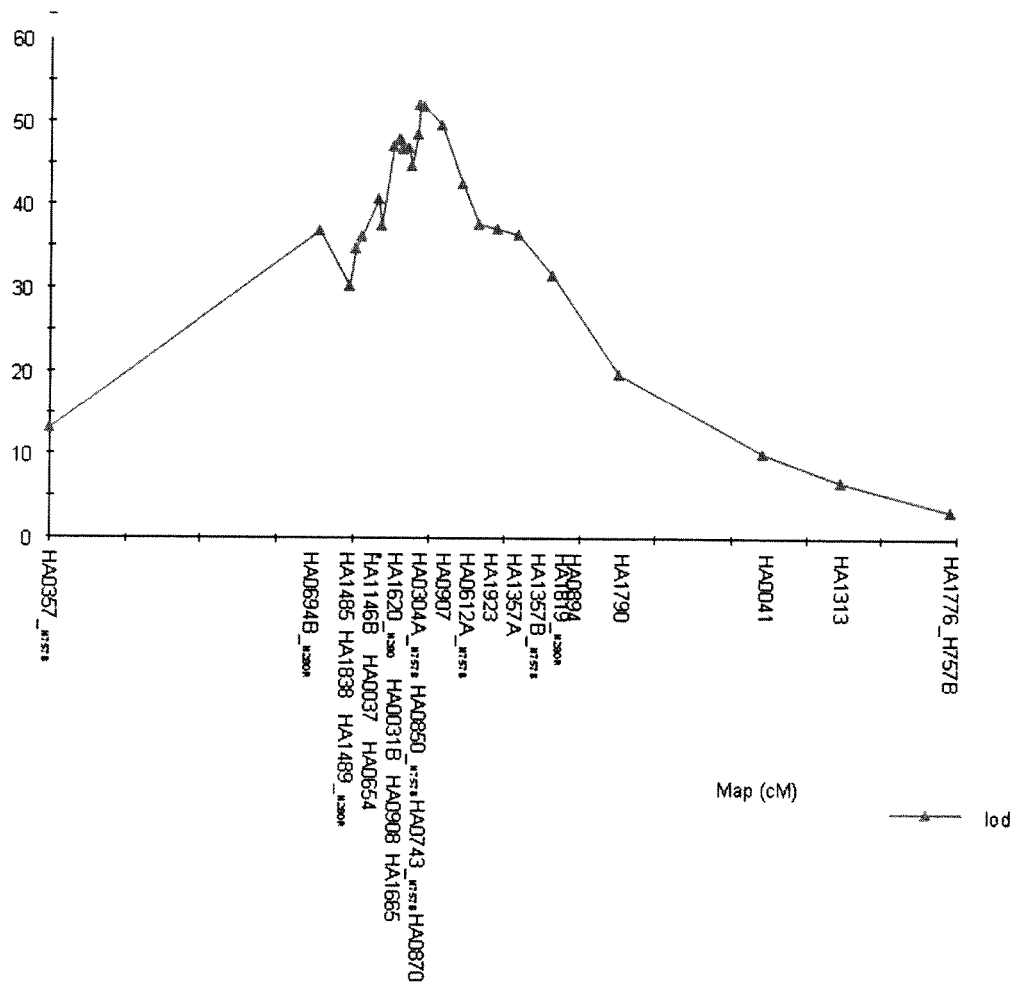
FIG. 5 includes a schematic representation of the linkage between the locus for low palmitic acid content and several SSR markers, showing the location of the major low palmitic acid QTL on LG5. The LOD score is provided on the y-axis, and distance of the marker from the locus in cM is provided on the x-axis. The LOD score is determined using the multiple interval protocol implemented by the Map QTL software program (J. W. Van Ooijen, M. P. Boer, R. C. Jansen, C. Maliepaard (2002) Map QTL 4.0: software for the calculation of QTL positions on genetic maps, *Plant Research International*, Wageningen, The Netherlands).

In some embodiments, a marker that is linked to a low palmitic acid content phenotype may be selected from the QTL markers of sunflower linkage group 5 that are illustrated in FIG. 4. In some embodiments, a marker that is linked to a low palmitic acid content phenotype may be selected from those markers that are located within about 10 cM of a QTL marker illustrated in FIG. 4. Thus, marker that is linked to a low palmitic acid content phenotype may be, for example, within 10 cM; 9 cM; 8 cM; 7 cM; 6 cM; 5 cM; 4 cM; 3 cM; 2 cM; 1 cM; 0.75 cM; 0.5 cM; 0.25 cM; or less, from a QTL marker illustrated in FIG. 4.

A plant breeder can advantageously use molecular markers to identify desired individuals by identifying marker alleles that show a statistically significant probability of co-segregation with a desired phenotype (e.g., low palmitic acid content), manifested as linkage disequilibrium. By identifying a molecular marker or clusters of molecular markers that co-segregate with a quantitative trait, the breeder is thus identifying a QTL. By identifying and selecting a marker allele (or desired alleles from multiple markers) that associates with the desired phenotype, the plant breeder is able to rapidly select the phenotype by selecting for the proper molecular marker allele (i.e., MAS). The more molecular markers that are placed on the genetic map, the more potentially useful that map becomes for conducting MAS.

Marker set: As used herein, a "set" of markers or probes refers to a specific collection of markers or probes (or data derived therefrom) that may be used to identify individuals comprising a trait of interest. In some embodiments, a set of markers linked to a low palmitic acid phenotype may be used to identify sunflower plants comprising low palmitic acid content. Data corresponding to a marker set or probe set (or data derived from the use of such markers or probes) may be stored in an electronic medium. While each marker in a marker set may possess utility with respect to trait identification, individual markers selected from the set and subsets including some, but not all, of the markers may also be effective in identifying individuals comprising the trait of interest.

Allele: As used herein, the term "allele" refers to one of two or more different nucleotide sequences that occur at a specific locus. For example, a first allele may occur on one chromosome, while a second allele may occur on a second homologous chromosome; e.g., as occurs for different chromosomes of a heterozygous individual, or between different homozygous or heterozygous individuals in a population. In some embodiments, a particular allele at a particular locus may be linked to an agronomically desirable phenotype (e.g., low palmitic acid content). In some embodiments, a particular allele at the locus may allow the identification of plants that do not comprise the agronomically desirable phenotype (e.g., high palmitic acid content plants), such that those plants may be removed from a breeding program or planting. A marker allele may segregate with a favorable phenotype, therefore providing the benefit of identifying plants comprising the phenotype. An "allelic form of a chromosome segment" may refer to a chromosome segment that comprises a marker allele nucleotide sequence that contributes to, or is linked to, a particular phenotype at one or more genetic loci physically located on the chromosome segment.

"Allele frequency" may refer to the frequency (expressed as a proportion or percentage) at which an allele is present at a locus within a plant, within a line, or within a population of lines. Thus, for an allele "A," a diploid individual of genotype "AA," "Aa," or "aa," has an allele frequency of 1.0, 0.5, or 0.0, respectively. The allele frequency within a line may be estimated by averaging the allele frequencies of a sample of individuals from that line. Similarly, the allele frequency within a population of lines may be calculated by averaging the allele frequencies of lines that make up the population. For a population with a finite number of individuals or lines, an allele frequency may be expressed as a count of individuals or lines (or any other specified grouping) containing the allele.

A marker allele "positively" correlates with a trait when the marker is linked to the trait, and when presence of the marker allele is an indicator that the desired trait or trait form will occur in a plant comprising the allele. A marker allele "negatively" correlates with a trait when the marker is linked to the trait, and when presence of the marker allele is an indicator that the desired trait or trait form will not occur in a plant comprising the allele.

A "homozygous" individual has only one form of allele at a given locus (e.g., a diploid plant has a copy of the same allele form at a particular locus for each of two homologous chromosomes). An individual is "heterozygous" if more than one allele form is present at the locus (e.g., a diploid individual has one copy of a first allele form and one copy of a second allele form at the locus). The term "homogeneity" refers to members of a group that have the same genotype (i.e., the same allele frequency) at one or more specific loci of interest. In contrast, the term "heterogeneity" refers to individuals within a group that differ in genotype at one or more specific loci of interest.

Any technique that may be used to characterize the nucleotide sequence at a locus may be used to identify a marker allele. Methods for marker allele detection include, for example and without limitation, molecular identification methods (e.g., amplification and detection of a marker amplicon). For example, an allelic form of an SSR marker, or of a SNP marker, may be detected by an amplification based technology. In a typical amplification-based detection method, a marker locus or a portion of the marker locus is amplified (using, e.g., PCR, LCR, and transcription using a nucleic acid isolated from a sunflower plant of interest as an amplification template), and the resulting amplified marker amplicon is detected. In some embodiments, plant RNA may be utilized as the template for an amplification reaction. In some embodiments, plant genomic DNA may be utilized as the template for the amplification reaction. In some examples, the QTL marker is an SNP marker, and the detected allele is a SNP marker allele, and the method of detection is allele specific hybridization (ASH). In some examples, the QTL marker is an SSR marker, and the detected allele is an SSR marker allele.

ASH technology is based on the stable annealing of a short, single-stranded, oligonucleotide probe to a completely complementary single-strand target nucleic acid. Detection may be accomplished via detection of an isotopic or non-isotopic label attached to the probe. For each polymorphism, two or more different ASH probes may be designed to have identical DNA sequences, except at site of a polymorphism. Each probe may be perfectly homologous with one allele sequence, so that the range of probes can distinguish all the known alternative allele sequences. When each probe is hybridized to target DNA under appropriate probe design and hybridization conditions, a single-base mismatch between the probe and target DNA prevents hybridization. In this manner, only one of the alternative probes will hybridize to a target sample that is homozygous for an allele. Samples that are heterozygous or heterogeneous for two alleles will hybridize to both of two alternative probes.

ASH markers may be used as dominant markers, where the presence or absence of only one allele is determined from hybridization or lack of hybridization by only one probe. The alternative allele may be inferred from a lack of hybridization. In examples, ASH probe and target molecules may be RNA or DNA molecules; a target molecule may comprise any length of nucleotides beyond the sequence that is complementary to the probe; the probe may be designed to hybridize with either strand of a DNA target; and the size of the probe may be varied to conform with the requirements of different hybridization conditions.

Amplified variable sequences refer to amplified sequences of the plant genome that exhibit high nucleic acid residue variability between members of the same species. All organisms have variable genomic sequences, and each organism (with the exception of a clone) has a different set of variable sequences. Once identified, the presence of specific variable sequence can be used to predict phenotypic traits. DNA from a plant may in some examples be used as a template for amplification with primers that flank a variable sequence of DNA. The variable sequence may be amplified and then sequenced.

Self-sustained sequence replication may also and alternatively be used to identify genetic markers. Self-sustained sequence replication refers to a method of nucleic acid amplification using target nucleic acid sequences that are replicated exponentially in vitro under substantially isothermal conditions, using three enzymatic activities involved in retroviral replication: reverse transcriptase; Rnase H; and a DNA-dependent RNA polymerase. Guatelli et al. (1990) Proc. Natl. Acad. Sci. USA 87:1874. By mimicking the retroviral strategy of RNA replication by means of cDNA intermediates, this reaction accumulates cDNA and RNA copies of the original target.

Data representing detected marker allele(s) may be transmitted (for example, electronically; and via infrared, wireless, or optical transmission) to a computer or computer-readable medium for analysis or storage.

For example, an amplification primer or amplification primer pair may be admixed with a genomic nucleic acid isolated from a first sunflower plant or germplasm, wherein the primer or primer pair is complementary or partially complementary to at least a portion of a marker locus, and the primer or primer pair is capable of initiating DNA polymerization by a DNA polymerase using the sunflower genomic nucleic acid as a template. The primer or primer pair (e.g., a primer pair provided in Table 6) is extended in a DNA polymerization reaction utilizing a DNA polymerase and a template genomic nucleic acid to generate at least one amplicon.

"Positional cloning" refers to a particular cloning procedure in which a target nucleic acid is identified and isolated by its genomic proximity to a marker. For example, a genomic nucleic acid clone may include all or part of two more chromosomal regions that are proximal to one another. If a marker can be used to identify the genomic nucleic acid clone from a genomic library, standard methods such as sub-cloning and/or sequencing may be used to identify and or isolate sub-sequences of the clone that are located near the marker.

Locus: As used herein, the term "locus" refers to a position on the genome that corresponds to a measurable characteristic (e.g., a trait) or polymorphism. An SNP locus is defined by a probe that hybridizes to DNA contained within the locus.

Marker-assisted breeding: As used herein, the term "marker-assisted breeding" may refer to an approach to breeding directly utilizing MAS for one or more traits (e.g., reduced palmitic acid content). In current practice, plant breeders attempt to identify easily detectable traits, such as flower color, seed coat appearance, or isozyme variants that are linked to an agronomically desired trait. The plant breeders then follow the agronomic trait in the segregating, breeding populations by following the segregation of the easily detectable trait. However, there are very few of these linkage relationships available for use in plant breeding.

Marker-assisted breeding provides a time- and cost-efficient process for improvement of plant varieties. Several examples of the application of marker-assisted breeding involve the use of isozyme markers. See, e.g., Tanksley and Orton, eds. (1983) *Isozymes in Plant Breeding and Genetics*, Amsterdam: Elsevier. One example is an isozyme marker associated with a gene for resistance to a nematode pest in tomato. The resistance, controlled by a gene designated Mi, is located on chromosome 6 of tomato and is very tightly linked to Aps1, an acid phosphatase isozyme. Use of the Aps1 isozyme marker to indirectly select for the Mi gene provided the advantages that segregation in a population can be determined unequivocally with standard electrophoretic techniques; the isozyme marker can be scored in seedling tissue, obviating the need to maintain plants to maturity; and co-dominance of the isozyme marker alleles allows discrimination between homozygotes and heterozygotes. See Rick (1983) in Tanksley and Orton, supra.

Probe: In some embodiments, the presence of a marker in a plant may be detected through the use of a nucleic acid probe. A probe may be a DNA molecule or an RNA molecule. RNA probes can be synthesized by means known in the art, for example, using a DNA molecule template. A probe may contain all or a portion of the nucleotide sequence of the marker and additional, contiguous nucleotide sequence from the plant genome. This is referred to herein as a "contiguous probe." The additional, contiguous nucleotide sequence is referred to as "upstream" or "downstream" of the original marker, depending on whether the contiguous nucleotide sequence from the plant chromosome is on the 5' or the 3' side of the original marker, as conventionally understood. As is recognized by those of ordinary skill in the art, the process of obtaining additional, contiguous nucleotide sequence for inclusion in a marker may be repeated nearly indefinitely (limited only by the length of the chromosome), thereby identifying additional markers along the chromosome.

An oligonucleotide probe sequence may be prepared synthetically or by cloning. Suitable cloning vectors are well-known to those of skill in the art. An oligonucleotide probe may be labeled or unlabeled. A wide variety of techniques exist for labeling nucleic acid molecules, including, for example and without limitation: radiolabeling by nick translation; random priming; tailing with terminal deoxytransferase, or the like, where the nucleotides employed are labeled, for example, with radioactive $^{32}P$. Other labels which may be used include, for example and without limitation: Fluorophores (e.g., FAM and VIC); enzymes; enzyme substrates; enzyme cofactors; enzyme inhibitors; and the like. Alternatively, the use of a label that provides a detectable signal, by itself or in conjunction with other reactive agents, may be replaced by ligands to which receptors bind, where the receptors are labeled (for example, by the above-indicated labels) to provide detectable signals, either by themselves, or in conjunction with other reagents. See, e.g., Leary et al. (1983) *Proc. Natl. Acad. Sci. USA* 80:4045-9.

A probe may contain a nucleotide sequence that is not contiguous to that of the original marker; this probe is referred to herein as a "noncontiguous probe." The sequence of the noncontiguous probe is located sufficiently close to the sequence of the original marker on the genome so that the noncontiguous probe is genetically linked to the same gene or trait (e.g., low palmitic acid content). For example, in some embodiments, a noncontiguous probe is located within about 10 cM; 9 cM; 8 cM; 7 cM; 6 cM; 5 cM; 4 cM; 3 cM; 2 cM; 1 cM; 0.75 cM; 0.5 cM; 0.25 cM; or less, from a QTL marker illustrated in FIG. 4.

A probe may be an exact copy of a marker to be detected. A probe may also be a nucleic acid molecule comprising, or consisting of, a nucleotide sequence which is substantially identical to a cloned segment of the subject organism's (e.g., sunflower) chromosomal DNA. As used herein, the term "substantially identical" may refer to nucleotide sequences that are more than 85% identical. For example, a substantially identical nucleotide sequence may be 85.5%; 86%; 87%; 88%; 89%; 90%; 91%; 92%; 93%; 94%; 95%; 96%; 97%; 98%; 99% or 99.5% identical to a reference sequence.

A probe may also be a nucleic acid molecule that is "specifically hybridizable" or "specifically complementary" to an exact copy of the marker to be detected ("DNA target"). "Specifically hybridizable" and "specifically complementary" are terms that indicate a sufficient degree of complementarity such that stable and specific binding occurs between the nucleic acid molecule and the DNA target. A nucleic acid molecule need not be 100% complementary to its target sequence to be specifically hybridizable. A nucleic acid molecule is specifically hybridizable when there is a sufficient degree of complementarity to avoid non-specific binding of the nucleic acid to non-target sequences under conditions where specific binding is desired, for example, under stringent hybridization conditions.

Hybridization conditions resulting in particular degrees of stringency will vary depending upon the nature of the hybridization method of choice and the composition and length of the hybridizing nucleic acid sequences. Generally, the temperature of hybridization and the ionic strength (especially the $Na^+$ and/or $Mg^{++}$ concentration) of the hybridization buffer will determine the stringency of hybridization, though wash times also influence stringency. Calculations regarding hybridization conditions required for attaining particular degrees of stringency are known to those of ordinary skill in the art, and are discussed, for example, in Sambrook et al. (ed.) *Molecular Cloning: A Laboratory Manual*, $2^{nd}$ ed., vol. 1-3, Cold Spring Harbor Laboratory Press, Cold Spring Harbor, N.Y., 1989, chapters 9 and 11; and Hames and Higgins (eds.) *Nucleic Acid Hybridization*, IRL Press, Oxford, 1985. Further detailed instruction and guidance with regard to the hybridization of nucleic acids may be found, for example, in Tijssen, "Overview of principles of hybridization and the strategy of nucleic acid probe assays," in *Laboratory Techniques in Biochemistry and Molecular Biology-Hybridization with Nucleic Acid Probes*, Part I, Chapter 2, Elsevier, N.Y., 1993; and Ausubel et al., Eds., *Current Protocols in Molecular Biology*, Chapter 2, Greene Publishing and Wiley-Interscience, NY, 1995.

As used herein, "stringent conditions" encompass conditions under which hybridization will only occur if there is less than 50% mismatch between the hybridization molecule and the DNA target. "Stringent conditions" include further particular levels of stringency. Thus, as used herein, "moderate stringency" conditions are those under which molecules with more than 50% sequence mismatch will not hybridize; conditions of "high stringency" are those under which sequences with more than 20% mismatch will not hybridize; and conditions of "very high stringency" are those under which sequences with more than 10% mismatch will not hybridize.

The following are representative, non-limiting hybridization conditions.

Very High Stringency (detects sequences that share at least 90% sequence identity): Hybridization in 5×SSC buffer at 65° C. for 16 hours; wash twice in 2×SSC buffer at room temperature for 15 minutes each; and wash twice in 0.5× SSC buffer at 65° C. for 20 minutes each.

High Stringency (detects sequences that share at least 80% sequence identity): Hybridization in 5×-6×SSC buffer at 65-70° C. for 16-20 hours; wash twice in 2×SSC buffer at room temperature for 5-20 minutes each; and wash twice in 1×SSC buffer at 55-70° C. for 30 minutes each.

Moderate Stringency (detects sequences that share at least 50% sequence identity): Hybridization in 6×SSC buffer at room temperature to 55° C. for 16-20 hours; wash at least twice in 2×-3×SSC buffer at room temperature to 55° C. for 20-30 minutes each.

With respect to all probes discussed, supra, the probe may comprise additional nucleic acid sequences, for example, promoters; transcription signals; and/or vector sequences. Any of the probes discussed, supra, may be used to define additional markers that are linked to a gene involved in reduced palmitic acid content in sunflower, and markers thus identified may be equivalent to exemplary markers named in the present disclosure, and thus are within the scope of the invention.

Sequence identity: The term "sequence identity" or "identity," as used herein in the context of two nucleic acid or polypeptide sequences, may refer to the residues in the two sequences that are the same when aligned for maximum correspondence over a specified comparison window.

As used herein, the term "percentage of sequence identity" may refer to the value determined by comparing two optimally aligned sequences (e.g., nucleic acid sequences) over a comparison window, wherein the portion of the sequence in the comparison window may comprise additions or deletions (i.e., gaps) as compared to the reference sequence (which does not comprise additions or deletions) for optimal alignment of the two sequences. The percentage is calculated by determining the number of positions at which the identical nucleotide or amino acid residue occurs in both sequences to yield the number of matched positions, dividing the number of matched positions by the total number of positions in the comparison window, and multiplying the result by 100 to yield the percentage of sequence identity.

Methods for aligning sequences for comparison are well-known in the art. Various programs and alignment algorithms are described in, for example: Smith and Waterman (1981) *Adv. Appl. Math.* 2:482; Needleman and Wunsch (1970) *J. Mol. Biol.* 48:443; Pearson and Lipman (1988) *Proc. Natl. Acad. Sci. U.S.A.* 85:2444; Higgins and Sharp (1988) *Gene* 73:237-44; Higgins and Sharp (1989) *CABIOS* 5:151-3; Corpet et al. (1988) *Nucleic Acids Res.* 16:10881-90; Huang et al. (1992) *Comp. Appl. Biosci.* 8:155-65; Pearson et al. (1994) *Methods Mol. Biol.* 24:307-31; Tatiana et al. (1999) *FEMS Microbiol. Lett.* 174:247-50. A detailed consideration of sequence alignment methods and homology calculations can be found in, e.g., Altschul et al. (1990) *J. Mol. Biol.* 215:403-10.

The National Center for Biotechnology Information (NCBI) Basic Local Alignment Search Tool (BLAST™; Altschul et al. (1990)) is available from several sources, including the National Center for Biotechnology Information (Bethesda, Md.), and on the internet, for use in connection with several sequence analysis programs. A description of how to determine sequence identity using this program is available on the internet under the "help" section for BLAST™. For comparisons of nucleic acid sequences, the "Blast 2 sequences" function of the BLAST™ (Blastn) program may be employed using the default BLOSUM62 matrix set to default parameters. Nucleic acid sequences with even greater similarity to the reference sequences will show increasing percentage identity when assessed by this method.

Nucleic acid molecule: As used herein, the term "nucleic acid molecule" may refer to a polymeric form of nucleotides, which may include both sense and anti-sense strands of RNA, cDNA, genomic DNA, and synthetic forms and mixed polymers of the above. A nucleotide may refer to a ribonucleotide, deoxyribonucleotide, or a modified form of either type of nucleotide. A "nucleic acid molecule" as used herein is synonymous with "nucleic acid" and "polynucleotide." The term includes single- and double-stranded forms of DNA. A nucleic acid molecule can include either or both naturally occurring and modified nucleotides linked together by naturally occurring and/or non-naturally occurring nucleotide linkages.

An "exogenous" molecule is a molecule that is not native to a specified system (e.g., a germplasm, variety, elite variety, and/or plant) with respect to nucleotide sequence and/or genomic location for a polynucleotide, and with respect to amino acid sequence and/or cellular localization for a polypeptide. In embodiments, exogenous or heterologous polynucleotides or polypeptides may be molecules that have been artificially supplied to a biological system (e.g., a plant cell, a plant gene, a particular plant species or variety, and/or a plant chromosome) and are not native to that particular biological system. Thus, the designation of a nucleic acid as "exogenous" may indicate that the nucleic acid originated from a source other than a naturally occurring source, or it may indicate that the nucleic acid has a non-natural configuration, genetic location, or arrangement of elements.

In contrast, for example, a "native" or "endogenous" nucleic acid is a nucleic acid (e.g., a gene) that does not contain a nucleic acid element other than those normally present in the chromosome or other genetic material on which the nucleic acid is normally found in nature. An endogenous gene transcript is encoded by a nucleotide sequence at its natural chromosomal locus, and is not artificially supplied to the cell.

The term "recombinant" refers to a material (e.g., recombinant nucleic acid, recombinant gene, recombinant polynucleotide, and/or recombinant polypeptide) that has been altered by human intervention. For example, the arrangement of the parts or elements of a recombinant molecule may not be a native arrangement, and/or the primary sequence of the recombinant molecule may been changed from its native sequence in some way. A material may be altered to produce a recombinant material within or removed from its natural environment or state. An open reading frame of a nucleic acid is recombinant if the nucleotide sequence of the open reading frame has been removed from it natural context and cloned into any type of artificial nucleic acid (e.g., a vector). Protocols and reagents to produce recombinant molecules, especially recombinant nucleic acids, are common and routine in the art. The term "recombinant" may also herein refer to a cell or organism that comprises recombinant material (e.g., a plant and/or plant cell that comprises a recombinant nucleic acid). In some examples, a recombinant organism is a transgenic organism.

As used herein, the term "introduced," when referring to translocation of a heterologous or exogenous nucleic acid into a cell, refers to the incorporation of the nucleic acid into the cell using any methodology available in the art. This term encompasses nucleic acid introduction methods including, for example and without limitation, transfection; transformation; and transduction.

As used herein, the term "vector" refers to a polynucleotide or other molecules that is capable of transferring at least one nucleic acid segment(s) into a cell. A vector may optionally comprise components/elements that mediate vector maintenance and enable its intended use (e.g., sequences necessary for replication, genes imparting drug or antibiotic resistance, a multiple cloning site, and/or operably linked promoter/enhancer elements that enable the expression of a cloned gene). Vectors may be derived, for example, from plasmids, bacteriophages, or plant or animal viruses. A "cloning vector," "shuttle vector," or "subcloning vector" generally comprises operably linked elements to facilitate cloning or subcloning steps (e.g., a multiple cloning site containing multiple restriction endonuclease sites).

The term "expression vector," as used herein, refers to a vector comprising operably linked polynucleotide sequences that may facilitate expression of a coding sequence in a particular host organism. For example, a bacterial expression vector may facilitate expression of a coding sequence in a bacterium. A plant expression vector may facilitate expression of a coding sequence in a plant cell. Polynucleotide sequences that facilitate expression in prokaryotes may include, for example and without limitation, a promoter; an operator; and a ribosome binding site. Eukaryotic expression vectors (e.g., a plant expression vector) comprise promoters, enhancers, termination, and polyadenylation signals (and other sequences) that are generally different from those used in prokaryotic expression vectors.

Single-nucleotide polymorphism: As used herein, the term "single-nucleotide polymorphism" (SNP) may refer to a DNA sequence variation occurring when a single nucleotide in the genome (or other shared sequence) differs between members of a species or paired chromosomes in an individual. Within a population, SNPs can be assigned a minor allele frequency that is the lowest allele frequency at a locus that is observed in a particular population. This is simply the lesser of the two allele frequencies for single-nucleotide polymorphisms. Different populations are expected to exhibit at least slightly different allele frequencies. Particular populations may exhibit significantly different allele frequencies. In some examples, markers linked to SCN resistance are SNP markers.

SNPs may fall within coding sequences of genes, non-coding regions of genes, or in the intergenic regions between genes. SNPs within a coding sequence will not necessarily change the amino acid sequence of the protein that is produced, due to degeneracy of the genetic code. An SNP in which both forms lead to the same polypeptide sequence is termed "synonymous" (sometimes called a silent mutation). If a different polypeptide sequence is produced, they are termed "non-synonymous." A non-synonymous change may either be missense or nonsense, where a missense change results in a different amino acid, and a nonsense change results in a premature stop codon. SNPs that are not in protein-coding regions may still have consequences for gene splicing, transcription factor binding, or the sequence of non-coding RNA. SNPs are usually biallelic and thus easily assayed in plants and animals. Sachidanandam (2001) *Nature* 409:928-33.

Plant: As used herein, the term "plant" may refer to a whole plant, a cell or tissue culture derived from a plant, and/or any part of any of the foregoing. Thus, the term "plant" encompasses, for example and without limitation, whole plants; plant components and/or organs (e.g., leaves, stems, and roots); plant tissue; seed; and a plant cell. A plant cell may be, for example and without limitation, a cell in and/or of a plant, a cell isolated from a plant, and a cell obtained through culturing of a cell isolated from a plant. Thus, the term "sunflower plant" may refer to, for example and without limitation, a whole sunflower plant; multiple sunflower plants; sunflower plant cell(s); sunflower plant protoplast; sunflower tissue culture (e.g., from which a sunflower plant can be regenerated); sunflower plant callus; sunflower plant parts (e.g., sunflower seed, sunflower flower, sunflower cotyledon, sunflower leaf, sunflower stem, sunflower bud, sunflower root, and sunflower root tip); and sunflower plant cells that are intact in sunflower plants or in parts of sunflower plants.

A "transgenic plant" is a plant comprising within at least one of its cells an exogenous polynucleotide. In examples, the exogenous polynucleotide is stably integrated within the genome of the cell, such that the polynucleotide may be inherited in successive generations. In some examples, the heterologous polynucleotide may be integrated into the genome as part of a recombinant expression cassette. The term "transgenic" is used herein to refer to any cell, cell line, callus, tissue, plant part, or plant, the genotype of which has been altered by the presence of a exogenous nucleic acid. Thus, this term encompasses transgenic organisms and cells that have been initially altered to comprise the exogenous polynucleotide, and those organisms and cells created by crosses or asexual propagation of the initial transgenic organism or cell. The term "transgenic," as used herein, does not encompass genome (chromosomal or extra-chromosomal) alternations introduced by conventional plant breeding methods (e.g., crosses of only non-transgenic organisms) or by naturally occurring events (e.g., random cross-fertilization, non-recombinant viral infection, non-recombinant bacterial transformation, non-recombinant transposition, and spontaneous mutation).

A plant "line," "variety," or "strain" is a group of individual plants having the same parentage. Plants of a line generally are inbred to some degree, and are generally homozygous and homogeneous at most genetic loci. A "subline" may refer to an inbred subset of descendents from a common progenitor that are genetically distinct from other similarly inbred subsets descended from the same progenitor. In some embodiments, a "subline" may be produced by inbreeding seed from an individual sunflower plant selected at the $F_3$ to $F_5$ generation until the residual segregating loci are homozygous across most or all loci.

Commercial sunflower varieties are typically produced by aggregating the self-pollinated progeny ("bulking") of a single $F_3$ to $F_5$ plant from a controlled cross between 2 genetically different parents. While such a variety typically appears uniform, a self-pollinating variety derived from the selected plant eventually (for example, by the $F_8$ generation) becomes a mixture of homozygous plants that may vary in genotype at any locus that was heterozygous in the originally selected $F_3$ to $F_5$ plant. In embodiments described herein, marker-based sublines that differ from each other based on qualitative marker polymorphism at the DNA level at one or more specific loci, are produced by genotyping a sample of seed derived from individual self-pollinated progeny derived from a selected $F_3$ to $F_5$ plant. Such a seed sample may be genotyped directly as seed, or as plant tissue grown from seed. In some examples, seed sharing a common genotype at one or more specified marker locus are bulked to produce a subline that is genetically homogenous at one or more locus that is linked to a trait of interest (e.g., low palmitic acid content).

An "ancestral line" refers to a parent line that is or has been used as a source of genetic material, for example, for the development of elite lines. An "ancestral population" refers to a group of ancestors that have contributed the bulk of the genetic variation that was used to develop an elite line. "Descendants" are progeny of ancestors, and descendents may be separated from their ancestors by many generations of breeding. For example, elite lines are the descendants of their ancestors. A pedigree may be used to describe the relationship between a descendant and each of its ancestors. A pedigree may span one or more generations, and thus may describe relationships between a descendant and its ancestors removed by 1, 2, 3, 4, etc., generations.

An "elite line" or "elite strain" refers to an agronomically superior line that has been bred and selected (often through many cycles) for superior agronomic performance. Numerous elite sunflower lines are available and known to those of skill in the art. An elite population is an assortment of elite lines or individuals from elite lines that may be used to represent the state of the art in terms of the available agronomically superior genotypes of a given crop species (e.g., sunflower). Similarly, an elite germplasm or elite strain of germplasm is an agronomically superior germplasm. An elite germplasm may be obtained from a plant with superior agronomic performance, and may capable of being used to generate a plant with superior agronomic performance, such as a sunflower of an existing or newly developed elite line.

In contrast to elite lines, an "exotic line" or "exotic strain" (or an "exotic germplasm") refers to a line or germplasm obtained from a sunflower not belonging to an available elite sunflower line or strain of germplasm. In the context of a cross between two sunflower plants or germplasms, an exotic germplasm is not closely related by descent to the elite germplasm with which it is crossed. Most commonly, exotic germplasm has been selected to introduce a novel genetic element (e.g., an allele form of interest) into a breeding program.

Trait or phenotype: The terms "trait" and "phenotype" are used interchangeably herein to refer to a measurable or observable heritable characteristic. A phenotype may in some examples be directly controlled by a single gene or genetic locus (i.e., a single gene trait). In other examples, a phenotype may be the result of an interaction between several genes (a complex trait). Thus, a QTL can act through a single gene mechanism or by a polygenic mechanism. In some examples, a trait or phenotype can be assigned a "phenotypic value," which corresponds to a quantitative value measured for the phenotypic trait.

The term "molecular phenotype" may refer to a phenotype that is detectable at the level of a population of (one or more) molecules. In some examples, the molecular phenotype may only be detectable at the molecular level. The detectable molecules of the phenotype may be nucleic acids (e.g., genomic DNA or RNA); proteins; and/or metabolites. For example, a molecular phenotype may be an expression profile for one or more gene products (e.g., at a specific stage of plant development, or in response to an environmental condition or stress).

Low palmitic acid content: For the purposes of the present disclosure, a trait of particular interest is "low palmitic acid content." Although the fatty acid composition of sunflower plants may be affected to an extent by environmental factors, those in the art understand that palmitic acid content (as well as other oil traits) are predominantly determined by heritable genetic factors. Thus, for example, the selection of a particular sunflower variety for cultivation may be based at least in part on the characteristic palmitic acid content of that particular variety under normal field growing conditions (e.g., conditions without drought, disease, and adequate soil nutrients). In examples, a sunflower plant having a low palmitic acid content may comprise a palmitic acid (16:0) content that is about 3% or less of the total oil content in seed of the plant. In some examples, such a sunflower plant having a low palmitic acid content comprises a palmitic acid content that is about 2.5% or less of the total oil content in seed of the plant, for example and without limitation, the palmitic acid content may be 2.6%; 2.5%; 2.4%; 2.3%; 2.2%; 2.1%; 2.0%; 1.9%; 1.8%; about 1.7%; and lower.

In some embodiments, "low palmitic acid content" is determined by comparison with the characteristic palmitic acid content of a wild-type or parental variety. Thus, a first sunflower comprising a low palmitic acid content phenotype may have "decreased" or "lowered" levels of palmitic acid relative to a wild-type sunflower, or relative to a parental sunflower variety from which the first sunflower was derived. Decreased and lowered are relative terms, indicating that the plant produces or contains less palmitic acid than a similar wild-type plant.

Sunflower plant palmitic acid content varies widely, and the characteristic palmitic acid contents measured in particular varieties represent a spectrum of higher and lower palmitic acid content phenotypes. However, by simple observation, the relative palmitic acid content of different plants, plant lines, or plant families may be determined. Furthermore, sunflower varieties represent genetically determinable phenotypic gradations of "palmitic acid content." One of skill in the art is familiar with assays for quantitating and scoring sunflower plant palmitic acid content. The palmitic acid content of a plant may be quantitated by using various analytical techniques standard in the art including, for example and without limitation, NMR; NIR; and Soxhlet extraction.

Verification of low palmitic acid content may be accomplished by using or adapting available palmitic acid content protocols. For example, NMR, NIR, and/or Soxhlet extraction may be utilized to verify that a low palmitic acid content trait still segregates with a particular marker in any particular plant or population. These and other protocols may also be used in some embodiments to measure the degree of palmitic acid content reduction achieved by introgressing or recombinantly introducing a marker linked to low palmitic acid content into a desired genetic background.

IV. Markers for Low Palmitic Acid Content in Sunflower

Embodiments of the invention include markers that are linked to low palmitic acid content in sunflower. Such markers may be used, for example and without limitation, to identify sunflower plants and germplasm having an increased likelihood of comprising a low palmitic acid phenotype; to select such sunflower plants and germplasm (e.g., in a marker-assisted selection program); and to identify and select sunflower plants and germplasm that do not have an increased likelihood of comprising a low palmitic acid phenotype. Use of one or more of the markers describe herein may provide advantages to plant breeders with respect to the time, cost, and labor involved in sunflower breeding, when compared to currently available compositions and methods in the art.

Disclosed herein are particular markers identified to be within or near a low palmitic acid content QTL region in linkage group 5 (LG5) in the sunflower genome that are polymorphic in parent genotypes. Among such QTL markers are particular marker alleles that are linked to a low palmitic acid content phenotype in sunflower. In some embodiments, a QTL marker that is linked to a low palmitic acid content phenotype in sunflower is selected from the subset of markers provided in FIG. 1. For example and without limitation, a QTL marker that is linked to a low palmitic acid content phenotype in sunflower may be selected from HA0031B; HA0908; HA1665; HA0304A; HA0850; HA0743; HA0870; HA0907; and HA0612A.

Mapping populations may be used to determine a marker that is linked to a low palmitic acid content. In some embodiments, such a mapping population may be derived from the cross, H757B/H280R, though other populations may also and alternatively be used. Any of many suitable software platforms may be used to determine a linked marker locus. For example and without limitation, TASSEL®; GeneFlow®; and MapManager-QTX® may be used in particular examples. In some embodiments, such as when software is used in a linkage analysis, data reflecting detected allele information may be electronically transmitted or electronically stored during use or prior to use, for example, in a computer readable medium.

In some embodiments, a first sunflower plant or germplasm that is likely to comprise a low palmitic acid content phenotype is identified by detecting a plurality of marker alleles in the first sunflower plant or germplasm. For example and without limitation, particular embodiments include methods for identifying plants or germplasm that is likely to comprise a low palmitic acid content phenotype, where a marker allele linked to low palmitic acid is detected from among the molecular markers, HA0031B; HA0908; HA1665; HA0304A; HA0850; HA0743; HA0870; HA0907; and HA0612A. Methods for identifying plants or germplasm that is likely to comprise a low palmitic acid content phenotype according to some embodiments comprise detecting more than one marker allele linked to low palmitic acid from among the molecular markers, HA0031B; HA0908; HA1665; HA0304A; HA0850; HA0743; HA0870; HA0907; and HA0612A. Particular embodiments include methods for identifying plants or germplasm that is likely to comprise a low palmitic acid content phenotype, where a marker allele is detected from among molecular markers that are linked to at least one marker linked to low palmitic acid selected from HA0031B; HA0908; HA1665; HA0304A; HA0850; HA0743; HA0870; HA0907; and HA0612A.

In some embodiments, a detected allele is an allele form that positively correlates with low palmitic acid content. Alternatively, an allele that is detected may be an allele form that negatively correlates with low palmitic acid content, in which case the allele may be counter-selected. In the case where more than one marker allele is selected for detection, an allele is selected for each of the markers; thus, two or more alleles are detected. In some examples, a marker may comprise more than one advantageous (e.g., positively correlated) allele form; in such an example, any of such advantageous allele forms can be detected.

Thus, a plurality of marker alleles may be simultaneously detected in a single plant, germplasm, or population of plants. In examples of such methods, a plant or germplasm may be selected that contains positively correlated alleles from more than one marker linked to low palmitic acid content. In particular examples, positively correlated alleles from more than one marker linked to low palmitic acid content may be introgressed into a target (e.g., recipient) sunflower germplasm. It will be appreciated by those of skill in the art that the simultaneous selection (and/or introgression) of positively correlated alleles from more than one low palmitic acid content marker in the same plant or germplasm may result in an additive (e.g., synergistic) phenotype in the plant or germplasm.

Although particular marker alleles may co-segregate with a low palmitic acid content phenotype, such marker loci are not necessarily part of a QTL locus contributing to (e.g., responsible for) the low palmitic acid content. For example, it is not a requirement that a co-segregating marker be comprised within a gene (e.g., as part of the gene open reading frame) that contributes to or imparts low palmitic acid content. The association between a specific marker allele with a low palmitic acid content phenotype may be due to the original "coupling" linkage phase between the co-segregating marker allele and a QTL low palmitic acid content allele in the ancestral sunflower line from which the low palmitic acid content allele originated. Eventually, with repeated recombination, crossing-over events between the co-segregating marker and QTL locus may change this orientation. Thus, a positively correlated marker allele may change through successive generations, depending on the linkage phase that exists within the low palmitic acid content parent used to create segregating populations. This fact does not reduce the utility of the marker for monitoring segregation of the phenotype; it only changes which marker allele form is positively (vs. negatively) correlated in a given segregating population.

When referring to the relationship between two genetic elements (e.g., a genetic element contributing to low palmitic acid content and a proximal marker), "coupling" phase linkage refers to the circumstance where the positively correlated allele at a low palmitic acid content QTL is physically associated on the same chromosome strand as the positively correlated allele of the respective linked marker locus. In "coupling phase," both alleles are inherited together by progeny that inherit that chromosome strand. In "repulsion" phase linkage, the positively correlated allele at a locus of interest (e.g., a QTL for low palmitic acid content) is physically linked with a normally negatively correlated allele at the proximal marker locus, and thus the two alleles that are normally positively correlated are not inherited together (i.e., the two loci are "out of phase" with each other).

As used herein, a "positively correlated" allele of a marker is that allele of the marker that co-segregates with a desired phenotype (e.g., low palmitic acid content) in the mapping populations described herein. However, in view of the foregoing, it will be understood that due to the possibility of repulsion phase linkage, other allele forms of the marker may be used equivalently in other embodiments involving different populations.

Similarly, a linked marker allele form that does not co-segregate with low palmitic acid content may also and alternatively be used in some embodiments, since such an allele form may be used to identify a plant that is not likely to comprise a low palmitic acid phenotype. For example, such an allele may be used for exclusionary purposes (e.g., counter-selection) during breeding to identify alleles that negatively correlate with low palmitic acid content, and/or to eliminate increased palmitic acid content plants or germplasm from subsequent rounds of breeding.

A QTL marker has a minimum of one positively correlated allele, although in some examples the QTL marker may have two or more positively correlated alleles found in the population. Any positively correlated allele of such a marker may be used, for example, for the identification and construction of low (e.g., decreased) palmitic acid content sunflower lines. In some examples, one, two, three, or more positively correlated allele(s) of different markers linked to low palmitic acid content are identified in (or introgressed into) a plant, and all or a subset of the positively correlated markers may be selected for or against during MAS. In some embodiments, at least one plant or germplasm is identified that has at least one such allele that positively correlates with a low palmitic acid content phenotype.

Marker loci are themselves traits, and may thus be analyzed according to standard linkage analysis, e.g., by tracking the marker loci during segregation. Therefore, in some embodiments, linkage between markers is determined, for example, where one cM is equal to a 1% chance that a first marker locus will be separated by crossing-over in a single generation from a second locus (which may be any other trait, (e.g., a second marker locus), or another trait locus that comprises or is comprised within a QTL).

Genetic markers that are linked to QTL markers (e.g., QTL markers provided in FIG. 1 and their equivalents) are particularly useful when they are sufficiently proximal (i.e., sufficiently tightly linked) to a given QTL marker, so that the genetic marker and the QTL marker display a low recombination frequency. In some embodiments, a linked marker and a QTL marker display a recombination frequency of about 10% or less (i.e., the given marker is within about 10 cM of the QTL). By definition, these linked loci will co-segregate at least 90% of the time. Indeed, the closer a marker is to a QTL marker, the more effective and advantageous that marker becomes as an indicator for the desired trait. Nonetheless, markers that are, for example, more than about 10 cM from a QTL may be useful, particularly when combined with other linked markers.

Thus, in some embodiments, linked loci such as a QTL marker locus and a second marker locus display an inter-locus recombination frequency of about 10% or less; for example and without limitation, about 9% or less, about 8% or less, about 7% or less, about 6% or less, about 5% or less, about 4% or less, about 3% or less, and about 2% or less. In some examples, the relevant loci (e.g., a marker locus and a target locus, such as a QTL) display a recombination a frequency of about 1% or less; for example and without limitation, about 0.75% or less, about 0.5% or less, and about 0.25% or less. Thus, loci may in particular embodiments be separated by about 10 cM; about 9 cM; about 8 cM; about 7 cM; about 6 cM; about 5 cM; about 4 cM; about 3 cM; about 2 cM; about 1 cM; about 0.75 cM; about 0.5 cM; about 0.25 cM; or less. In some examples, specific linked markers may be determined by review of a genetic map of the sunflower genome including, for example, LG5.

In some aspects, linkage may be expressed as a recombination frequency limit, or as a genetic or physical distance range. For example, in some embodiments, two linked loci are two loci that are separated by less than 50 cM map units. In some examples, linked loci are two loci that are separated by less than 40 cM. In some examples, two linked loci are two loci that are separated by less than 30 cM. In some examples, two linked loci are two loci that are separated by less than 25 cM. In some examples, two linked loci are two loci that are separated by less than 20 cM. In some examples, two linked loci are two loci that are separated by less than 15 cM. In some examples, linkage may be expressed as a range with an upper and a lower limit; for example and without limitation, between about 10 and 20 cM; between about 10 and 30 cM; between about 10 and 40 cM; between about 0.5 and about 10 cM; between about 0.1 and about 9 cM; between about 0.1 and about 8 cM; between about 0.1 and about 7 cM; between about 0.1 and about 6 cM; between about 0.1 and about 5 cM; between about 0.1 and about 4 cM; between about 0.1 and about 3 cM; between about 0.1 and about 2 cM; between about 0.1 and about 1 cM; and between about 0.1 and about 0.5 cM.

Markers described herein (e.g., those markers set forth in FIG. 1, HA0031B, HA0908, HA1665, HA0304A, HA0850, HA0743, HA0870, HA0907, HA0612A, and markers linked to at least one of the foregoing) are positively correlated with low sunflower palmitic acid content in some embodiments. Thus, these markers may be sufficiently proximal to a low palmitic acid content QTL and/or trait that one or more of the markers may be used as a predictor for a low palmitic acid content trait. This predictive ability is extremely useful in the context of MAS, as discussed in more detail herein.

Use of particular markers described herein that are linked to a low palmitic acid content phenotype and/or QTL marker is not restricted to any particular sunflower genetic map or methodology. It is noted that lists of linked markers may vary between maps and methodologies due to various factors. For example, the markers that are placed on any two maps may not be identical, and a first map may have a greater marker density than another, second map. Also, the mapping populations, methodologies, and algorithms used to construct genetic maps may differ. One of skill in the art recognizes that one genetic map is not necessarily more or less accurate than another, and the skilled person furthermore recognizes that any sunflower genetic map may be used to determine markers that are linked to a particular marker. For example, particular linked markers can be determined from any genetic map known in the art (e.g., an experimental map or an integrated map), and can be determined from any new mapping dataset.

Embodiments of the present invention are not limited to any particular sunflower population or use of any particular methodology (e.g., any particular software or any particular set of software parameters) to identify or determine linkage of a particular marker with a low palmitic acid content phenotype. In view of the present disclosure, one of ordinary skill in the art will be able to extrapolate features of the markers described herein to any sunflower gene pool or population of interest, and use any particular software and software parameters in so doing.

V. Detection of Markers for Low Palmitic Acid Content in Sunflower

Methods for detecting (identifying) sunflower plants or germplasm that carry particular alleles of low palmitic acid content marker loci are a feature of some embodiments. In some embodiments, any of a variety of marker detection protocols available in the art may be used to detect a marker allele, depending on the type of marker being detected. In examples, suitable methods for marker detection may include amplification and identification of the resulting amplified marker by, for example and without limitation, PCR; LCR; and transcription-based amplification methods (e.g., ASH, SSR detection, RFLP analysis, and many others).

In general, a genetic marker relies on one or more property of nucleic acids for its detection. For example, some techniques for detecting genetic markers utilize hybridization of a probe nucleic acid to a nucleic acid corresponding to the genetic marker (e.g., an amplified nucleic acid produced using a genomic sunflower DNA molecule as a template). Hybridization formats including, for example and without limitation, solution phase; solid phase; mixed phase; and in situ hybridization assays may be useful for allele detection in particular embodiments. An extensive guide to the hybridization of nucleic acids may be found, for example, in Tijssen (1993) *Laboratory Techniques in Biochemistry and Molecular Biology-Hybridization with Nucleic Acid Probes* Elsevier, N.Y.

Markers corresponding to genetic polymorphisms between members of a population may be detected by any of numerous methods including, for example and without limitation, nucleic acid amplification-based methods; and nucleotide sequencing of a polymorphic marker region. Many detection methods (including amplification-based and sequencing-based methods) may be readily adapted to high throughput analysis in some examples, for example, by using available high throughput sequencing methods, such as sequencing by hybridization.

Amplification primers for amplifying SSR-type marker loci are included in particular examples of some embodiments. Table 6 provides specific primers for amplification of particular markers described herein. However, one of skill will immediately recognize that other sequences on either side of the given primers may be used in place of the given primers, so long as the primers are capable of amplifying a nucleotide sequence comprising the allele to be detected. Further, the precise probe used for allele detection may vary. For example, any probe capable of identifying the region of a marker amplicon to be detected may be substituted for the exemplary probes listed herein. Further, the configuration of amplification primers and detection probes may also vary. Thus, embodiments are not limited to the primers and probes specifically recited herein. Although many specific examples of primers are provided herein (see Table 6), suitable primers to be used with the invention may be designed using any suitable method. For example, equivalent primers may be designed using any suitable software program, such as for example and without limitation, LASERGENE®.

Molecular markers may be detected by established methods available in the art including, for example and without limitation: ASH, or other methods for detecting SNPs; AFLP detection; amplified variable sequence detection; RAPD detection; RFLP detection; self-sustained sequence replication detection; SSR detection; SSCP detection; and isozyme markers detection. While the exemplary markers provided in FIG. 1 and Table 6 are SSR markers, any of the aforementioned marker types may be employed in particular embodiments to identify chromosome segments encompassing a genetic element that contributes to a low palmitic acid content phenotype in sunflower.

For example, markers that comprise RFLPs may be detected, for example, by hybridizing a probe (which is typically a sub-fragment or synthetic oligonucleotide corresponding to a sub-fragment) of the nucleic acid to be detected to restriction-digested genomic DNA. The restriction enzyme is selected so as to provide restriction fragments of at least two alternative (or polymorphic) lengths in different individuals or populations. Determining one or more restriction enzyme(s) that produces informative fragments for each cross is a simple procedure that is easily accomplished by those of skill in the art after provision of the target DNA sequence. After separation by length in an appropriate matrix (e.g., agarose or polyacrylamide) and transfer to a membrane (e.g., nitrocellulose or nylon), a labeled probe may be hybridized under conditions that result in equilibrium binding of the probe to the target, followed by removal of excess probe by washing, and detection of the labeled probe.

In some embodiments, an amplification step is utilized as part of a method to detect/genotype a marker locus. However, an amplification step is not in all cases a requirement for marker detection. For example, an unamplified genomic DNA may be detected simply by performing a Southern blot on a sample of genomic DNA. Separate detection probes may also be omitted in amplification/detection methods, for example and without limitation, by performing a real time amplification reaction that detects product formation by modification of an amplification primer upon incorporation into a product; incorporation of labeled nucleotides into an amplicon; and by monitoring changes in molecular rotation properties of amplicons as compared to unamplified precursors (e.g., by fluorescence polarization).

PCR, RT-PCR, real-time PCR, and LCR are in particularly broad use as amplification and amplification-detection methods for amplifying and detecting nucleic acids (e.g., those comprising marker loci). Details regarding the use of these and other amplification methods can be found in any of a variety of standard texts including, for example, Sambrook et al., *Molecular Cloning: A Laboratory Manual* (2000) 3rd Ed., Vol. 1-3, Cold Spring Harbor Laboratory, Cold Spring Harbor, N.Y.; *Current Protocols in Molecular Biology* (supplemented through 2002) F. M. Ausubel et al., eds., *Current Protocols*, a joint venture between Greene Publishing Associates, Inc. and John Wiley & Sons, Inc.; and *PCR Protocols A Guide to Methods and Applications* (1990) Innis et al. eds) Academic Press Inc., San Diego, Calif. Additional details regarding detection of nucleic acids in plants can also be found, for example, in *Plant Molecular Biology* (1993) Croy (ed.) BIOS Scientific Publishers, Inc.

Additional details regarding techniques sufficient to direct persons of skill through particular in vitro amplification and detection methods, including the polymerase chain reaction (PCR), the ligase chain reaction (LCR), Qβ-replicase amplification, and other RNA polymerase-mediated techniques (e.g., NASBA), and examples thereof, may also be found in, for example: U.S. Pat. No. 4,683,202; Arnheim and Levinson (1991) *J. NIH Res.* 3:81-94; Kwoh et al. (1989) *Proc. Natl. Acad. Sci. USA* 86:1173; Guatelli et al. (1990), supra; Lomeli et al. (1989) *J. Clin. Chem.* 35:1826; Landegren et al. (1988) *Science* 241:1077-80; Van Brunt (1990) *Biotechnology* 8:291-4; Wu and Wallace (1989) *Gene* 4:560; Barringer et al. (1990) *Gene* 89:117; and Sooknanan and Malek (1995) *Biotechnology* 13:563-4. Improved methods of amplifying large nucleic acids by PCR, which may be useful in some applications of positional cloning, are further described in Cheng et al. (1994) *Nature* 369:684, and the references cited therein, in which PCR amplicons of up to 40 kb are generated.

Many available biology texts also have extended discussions regarding PCR and related amplification methods. One of skill will appreciate that essentially any RNA can be converted into a double-stranded DNA that is suitable for restriction digestion, PCR amplification, and sequencing using reverse transcriptase and a polymerase (e.g., by RT-PCR).

In some embodiments, a nucleic acid probe may be used to detect a nucleic acid that comprises a marker allele nucleotide sequence. Such probes can be used, for example, in positional cloning to isolate nucleotide sequences that are linked to a marker allele sequence. Nucleic acid probes that are useful in particular embodiments are not limited by any particular size constraint. In some embodiments, a nucleic acid probe may be, for example and without limitation, at least 20 nucleotides in length; at least 50 nucleotides in length; at least 100 nucleotides in length; and at least 200 nucleotides in length. Nucleic acid probes to a marker locus may be cloned and/or synthesized.

Any suitable label may be used with a probe in particular examples. Detectable labels suitable for use with nucleic acid probes include any composition detectable by spectroscopic, radioisotopic, photochemical, biochemical, immunochemical, electrical, optical, or chemical means. Thus, a hybridized probe may be detected using, for example, autoradiography, fluorography, or other similar detection techniques, depending on the particular label to be detected. Useful labels include biotin (for staining with labeled streptavidin conjugate), magnetic beads, fluorescent dyes, radiolabels, enzymes, and colorimetric labels. Other labels include ligands that bind to antibodies or specific binding targets labeled with fluorophores, chemiluminescent agents, and enzymes. A probe may also comprise radiolabeled PCR primers that are used to generate a radiolabeled amplicon. Additional information regarding labeling strategies for labeling nucleic acids, and corresponding detection strategies may be found, for example, in Haugland (1996) *Handbook of Fluorescent Probes and Research Chemicals*, Sixth Edition, Molecular Probes, Inc., Eugene Oreg.; and Haugland (2001) *Handbook of Fluorescent Probes and Research Chemicals*, Eighth Edition, Molecular Probes, Inc., Eugene, Oreg. (Available on CD ROM). In particular examples, PCR detection and quantification is carried out using dual-labeled fluorogenic oligonucleotide probes, for example, TaqMan® probes (Applied Biosystems).

In some embodiments, primers are not labeled, and marker PCR amplicons may be visualized, for example, following their size resolution (e.g., following agarose gel electrophoresis). In particular examples, ethidium bromide staining of PCR amplicons following size resolution allows visualization of differently size amplicons corresponding to different marker alleles.

Primers for use in embodiments are not limited to those capable of generating an amplicon of any particular size. For example, primers used to amplify particular marker loci and alleles are not limited to those amplifying the entire region of the relevant locus. The primers may generate an amplicon of any suitable length that is longer or shorter than those given in the allele definitions. In examples, marker amplification may produce an amplicon that is, for example and without limitation, at least 20 nucleotides in length; at least 50 nucleotides in length; at least 100 nucleotides in length; and at least 200 nucleotides in length.

Synthetic methods for making oligonucleotides and useful compositions comprising oligonucleotides (e.g., probes, primers, molecular beacons, PNAs, and LNAs) are generally well-known by those of skill in the art. For example, oligonucleotides may be synthesized chemically according to the solid phase phosphoramidite triester method described in, for example, Beaucage and Caruthers (1981) *Tetrahedron Letts.* 22(20):1859-62. Such methods may employ an automated synthesizer, for example and without limitation, as described in Needham-VanDevanter et al. (1984) *Nucleic Acids Res.* 12:6159-68. Oligonucleotides (including modified oligonucleotides) may also be ordered from a variety of commercial sources including, for example and without limitation, The Midland Certified Reagent Company; The Great American Gene Company; ExpressGen Inc.; and Operon Technologies Inc. Similarly, PNAs may be custom ordered from any of a variety of sources including, for example and without limitation, PeptidoGenic; HTI Bio-Products, Inc.; BMA Biomedicals Ltd (U.K.); and Bio. Synthesis, Inc.

In some embodiments, an in silico method may be used to detect a marker allele. For example, the sequence of a nucleic acid comprising a marker sequence may be stored in a computer. The desired marker locus sequence (or its homolog) may be identified using an appropriate nucleic acid search algorithm, as provided by, for example and without limitation, BLAST™, or even simple word processors.

In some embodiments, a marker allele is detected using a PCR-based detection method, where the size or sequence of a PCR amplicon comprising the marker is indicative of the absence or presence of a particular marker allele. In some examples, PCR primers are hybridized to conserved regions flanking the polymorphic marker region. PCR primers so used to amplify a molecular marker are sometimes referred to in the art as "PCR markers," or simply "markers."

A primary motivation for development of molecular markers in crop species is the potential for increased efficiency in plant breeding through marker assisted selection (MAS). Genetic markers that are linked to a trait or gene of interest may be used to identify plants that contain a desired marker allele at one or more loci, which plants are thus expected to transfer the desired marker allele, along with the trait or gene of interest, to their progeny. Genetic markers may be used to identify plants that contain a particular genotype at one locus, or at several unlinked or linked loci (e.g., a haplotype). Similarly, marker alleles described herein may be introgressed into any desired sunflower genetic background, germplasm, plant, line, variety, etc., as part of an overall MAS breeding program designed to enhance sunflower yield.

According to some embodiments, markers described herein provide the means to identify sunflower plants and germplasm that comprise a low or reduced palmitic acid content (or high or increased palmitic acid content) by identifying plants and germplasm comprising a specific allele at a locus such as HA0031B, HA0908, HA1665, HA0304A, HA0850, HA0743, HA0870, HA0907, HA0612A, and a marker locus linked to at least one of the foregoing. By identifying plants lacking a marker allele that co-segregates with low palmitic acid, high palmitic acid plants and germplasm (or plants with a lesser decrease of palmitic acid content) may be identified, for example, for elimination from subsequent crosses and breeding.

According to the foregoing, embodiments of the invention include molecular markers that have a significant probability of co-segregation with a QTL that contributes to or imparts a low (e.g., decreased) palmitic acid content phenotype. These QTL markers find use in marker assisted selection for desired traits (decreased palmitic acid content), and also have other uses. Embodiments of the invention are not limited to any particular method for the detection or analysis of these markers.

VI. Introgression of Markers for Low Palmitic Acid Content into Sunflower Lines

As set forth, supra, identification of sunflower plants or germplasm that includes a marker allele or alleles that is/are linked to a low (e.g., decreased) palmitic acid content phenotype provides a basis for performing marker assisted selection of sunflower. In some embodiments, at least one sunflower plant that comprises at least one marker allele that is positively correlated with low palmitic acid is selected, while sunflower plants that comprise marker alleles that are negatively correlated with low palmitic acid content may be selected against.

Desired marker alleles that are positively correlated with low palmitic acid may be introgressed into sunflower having a particular (e.g., elite or exotic) genetic background, so as to produce an introgressed low palmitic acid content sunflower plant or germplasm. In some embodiments, a plurality of low palmitic acid content markers may be sequentially or simultaneous selected and/or introgressed into sunflower. The particular combinations of low palmitic acid content markers that may be selected for in a single plant or germplasm is not limited, and can include a combination of markers such as those set forth in FIG. 1, any markers linked to the markers recited in FIG. 1, or any markers located within the QTL intervals defined herein.

In embodiments, the ability to identify QTL marker alleles that are positively correlated with low palmitic acid content of a sunflower plant provides a method for selecting plants that have favorable marker loci as well. For example, any plant that is identified as comprising a desired marker allele (e.g., a marker allele that positively correlates with low palmitic acid content) may be selected for, while plants that lack the allele (or that comprise an allele that negatively correlates with low palmitic acid content) may be selected against. Thus, in particular embodiments, subsequent to identification of a marker allele in a first plant or germplasm, an introgression method includes selecting the first sunflower plant or germplasm, or selecting a progeny of the first plant or germplasm. In some examples, the resulting selected sunflower plant or germplasm may be crossed with a second sunflower plant or germplasm (e.g., an elite sunflower or an exotic sunflower), so as to produce progeny comprising the marker allele and desirable characteristics and/or alleles of the second plant or germplasm.

In some embodiments, a method of introgressing a low palmitic acid QTL may include, for example, providing at least one marker linked to low palmitic acid (e.g., a marker that co-segregates with low palmitic acid); determining the marker allele in a first plant or germplasm comprising a low palmitic acid QTL; and introgressing the marker allele into a second sunflower plant or germplasm, so as to produce an introgressed sunflower plant or germplasm. In particular embodiments, the second sunflower plant or germplasm may comprise increased palmitic acid content as compared to the first sunflower plant or germplasm, while the introgressed sunflower plant or germplasm will comprise a decreased palmitic acid content as compared to the second plant or germplasm. As discussed in more detail below, an introgressed sunflower plant or germplasm produced by these and other embodiments are also included in embodiments of the invention.

In some embodiments, where an introgressed sunflower plant or germplasm is produced by any of the methods provided herein, the introgressed sunflower plant or germplasm may be characterized by the fatty acid composition of the oil in seed from the plant. An introgressed plant or germplasm may comprise, for example and without limitation, about 3% or less palmitic acid in seed oil from the plant. In some examples, such an introgressed sunflower plant or germplasm comprises about 2.5% or less palmitic acid in seed oil from the plant, such as for example and without limitation, 2.6%; 2.5%; 2.4%; 2.3%; 2.2%; 2.1%; 2.0%; 1.9%; 1.8%; about 1.7%; and lower.

In addition to introgressing selected marker alleles (e.g., through standard breeding methods) into desired genetic backgrounds, so as to introgress a low palmitic acid QTL into the background, transgenic approaches may be used in some embodiments to produce low palmitic acid content sunflower plants and/or germplasm. In some embodiments, an exogenous nucleic acid (e.g., a gene or open reading frame) that is linked to at least one marker described herein in sunflower may be introduced into a target plant or germplasm. For example, a nucleic acid coding sequence linked to at least one marker described herein may be cloned from sunflower genomic DNA (e.g., via positional cloning) and introduced into a target plant or germplasm.

Thus, particular embodiments include methods for producing a sunflower plant or germplasm comprising a low palmitic acid content phenotype, wherein the method comprises introducing an exogenous nucleic acid into a target sunflower plant or progeny thereof, wherein the exogenous nucleic acid is substantially identical to a nucleotide sequence that is linked to at least one positively correlated marker allele at one or more marker locus that is linked to low palmitic acid content. In some examples, the marker locus may be selected from: HA0031B; HA0908; HA1665; HA0304A; HA0850; HA0743; HA0870; HA0907; HA0612A; and a marker that is linked (e.g., demonstrating not more than 10% recombination frequency) to at least one of the foregoing. In some embodiments, a plurality of linked markers may be used to construct a transgenic plant. Which of the markers described herein that are used in such a plurality is within the discretion of the practitioner.

Any of a variety of methods can be used to provide an exogenous nucleic acid to a sunflower plant or germplasm. In some embodiments, a nucleotide sequence is isolated by positional cloning, and is identified by linkage to a marker allele that is positively correlated with low palmitic acid content. For example, the nucleotide sequence may correspond to an open reading frame (ORF) that encodes a polypeptide that, when expressed in a sunflower plant, results in or contributes to the sunflower plant having low palmitic acid content. The nucleotide sequence may then be incorporated into an exogenous nucleic acid molecule. The precise composition of the exogenous nucleic acid may vary. For example, an exogenous nucleic acid may comprise an expression vector to provide for expression of the nucleotide sequence in the plant wherein the exogenous nucleic acid is introduced.

Markers linked to low palmitic acid content may be introgressed (for example, thereby introgressing a low palmitic acid content phenotype) into a sunflower plant or germplasm utilizing a method comprising marker assisted selection. In embodiments, MAS is performed using polymorphic markers that have been identified as having a significant likelihood of co-segregation with a low palmitic acid content trait. Such markers (e.g., those set forth in FIG. 1) are presumed to map within or near a gene or genes that contribute to the decreased palmitic acid content of the plant (compared to a plant comprising the wild-type gene or genes). Such markers may be considered indicators for the trait, and may be referred to as QTL markers. In embodiments, a plant or germplasm is tested for the presence of a positively correlated allele in at least one QTL marker.

In embodiments, linkage analysis is used to determine which polymorphic marker allele demonstrates a statistical likelihood of co-segregation with a low palmitic acid content phenotype. Following identification of such a positively correlated marker allele for the low palmitic acid content phenotype, the marker may then be used for rapid, accurate screening of plant lines for the low palmitic acid content allele without the need to grow the plants through their life cycle and await phenotypic evaluations. Furthermore, the identification of the marker permits genetic selection for the particular low palmitic acid content allele, even when the molecular identity of the actual low palmitic acid content QTL is unknown. A small tissue sample (for example, from the first leaf of the plant) may be taken from a progeny sunflower plant produced by a cross and screened with the appropriate molecular marker. Thereby, it may be rapidly determined whether the progeny should be advanced for further breeding. Linked markers also remove the impact of environmental factors that may influence phenotypic expression, thereby allowing the selection for low palmitic acid content sunflower in an environmental neutral manner. Therefore, while the contributions of various environmental factors to the oil traits of plants may appear at first glance to confound the use of the markers described herein, in fact a particular advantage of these markers is that they do not depend on environment for their utility.

In some embodiments comprising MAS, a polymorphic QTL marker locus may be used to select a plant that contains a marker allele (or alleles) that is positively correlated with a low palmitic acid content phenotype. For example, a nucleic acid corresponding to the marker nucleic acid allele may be detected in a biological sample from the plant to be selected. This detection may take the form of hybridization of a probe nucleic acid to a marker allele or amplicon thereof (e.g., using allele-specific hybridization, Southern analysis, northern analysis, in situ hybridization, and hybridization of primers followed by PCR amplification of a region of the marker). After the presence (or absence) of the particular marker allele in the biological sample is verified, the plant is selected, and may in some examples be used to make progeny plants by selective breeding.

Sunflower plant breeders desire combinations of low palmitic acid content marker loci with markers/genes other desirable traits (e.g., high yield) to develop improved sunflower varieties. Screening large numbers of samples by non-molecular methods (e.g., trait evaluation in sunflower plants) is generally expensive, time consuming, and unreliable. Use of the polymorphic markers described herein, which are linked to low palmitic acid content QTL, provides an effective method for selecting desirable varieties in breeding programs. Advantages of marker-assisted selection over field evaluations for low palmitic acid content include, for example, that MAS can be done at any time of year, regardless of the growing season. Moreover, as set forth, supra, environmental effects are largely irrelevant to marker-assisted selection.

When a population is segregating for multiple marker loci linked to one or more traits (e.g., multiple markers linked to low palmitic acid content), the efficiency of MAS compared to phenotypic screening becomes even greater, because all of the marker loci may be evaluated in the lab together from a single sample of DNA. In particular embodiments of the invention, the HA0031B, HA0908, HA1665, HA0304A, HA0850, HA0743, HA0870, HA0907, and HA0612A markers, as well as markers linked to at least one of the foregoing, may be assayed simultaneously or sequentially from a single sample, or from a plurality of parallel samples.

Another use of MAS in plant breeding is to assist the recovery of the recurrent parent genotype by backcross breeding. Backcrossing is usually performed for the purpose of introgressing one or a few markers or QTL loci from a donor parent (e.g., a parent comprising desirable low palmitic acid content marker loci) into an otherwise desirable genetic background from a recurrent parent (e.g., an otherwise high yielding sunflower line). The more cycles of backcrossing that are done, the greater the genetic contribution of the recurrent parent to the resulting introgressed variety. In some examples, many cycles of backcrossing may be carried out, for example, because low palmitic acid content plants may be otherwise undesirable, e.g., due to low yield, low fecundity, etc. In contrast, strains which are the result of intensive breeding programs may have excellent yield, fecundity, etc., merely being deficient in one desirable respect, such as palmitic acid content. In marker assisted backcrossing of specific markers from a donor source, which may or may not constitute an elite genetic background to an elite variety that will serve as the recurrent line, the practitioner may select among backcross progeny for the donor marker, and then use repeated backcrossing to the recurrent line to reconstitute as much of the recurrent line's genome as possible.

According to the foregoing, markers and methods described herein may be utilized to guide marker assisted selection or breeding of sunflower varieties with the desired complement (set) of allelic forms of chromosome segments associated with superior agronomic performance (e.g., low palmitic acid content, along with any other available markers for yield, disease resistance, etc.). Any of the described marker alleles may be introduced into a sunflower line via introgression (e.g., by traditional breeding, via transformation, or both) to yield a sunflower plant with superior agronomic performance. If nucleic acids from a plant are positive for a desired genetic marker allele, the plant may be self-fertilized in some embodiments to create a true breeding line with the same genotype, or it may be crossed with a plant comprising the same marker allele, or other desired markers and/or characteristics to create a sexually crossed hybrid generation.

Often, a method of the present invention is applied to at least one related sunflower plant such as from progenitor or descendant lines in the subject sunflower plants pedigree such that inheritance of the desired decreased palmitic acid content allele can be traced. The number of generations separating the sunflower plants being subject to the methods of the present invention will generally be from 1 to 20, commonly 1 to 5, and typically 1, 2, or 3 generations of separation, and quite often a direct descendant or parent of the sunflower plant will be subject to the method (i.e., one generation of separation).

Genetic diversity is important in breeding programs. With limited diversity, the genetic gain achieved in a breeding program will eventually plateau when all of the favorable alleles have been fixed within the elite population. Therefore, one objective of plant breeding is to incorporate diversity into an elite pool without losing the genetic gain that has already been made, and with the minimum possible investment. MAS provide an indication of which genomic regions, and which favorable alleles from the original ancestors, have been selected for and conserved over time, facilitating efforts to incorporate favorable variation from exotic germplasm sources (parents that are unrelated to the elite gene pool) in the hopes of finding favorable alleles that do not currently exist in the elite gene pool. Thus, in some embodiments, markers described herein may be used for MAS in crosses involving (elite×exotic) sunflower lines by subjecting segregating progeny to MAS to maintain major yield alleles, along with the decreased palmitic acid content marker alleles herein.

The molecular marker loci and alleles described herein (e.g., HA0031B, HA0908, HA1665, HA0304A, HA0850, HA0743, HA0870, HA0907, HA0612A, and markers linked to at least one of the foregoing) may be used in some embodiments, as indicated previously, to identify a low palmitic acid content QTL, which may then be cloned by familiar procedures. Such decreased low acid content clones may be first identified by their genetic linkage to markers described herein. For example, "positional gene cloning" takes advantage of the physical proximity of a low palmitic acid content marker to define an isolated chromosomal fragment containing a low palmitic acid content QTL gene. The isolated chromosomal fragment may be produced by such well-known methods as, for example and without limitation, digesting chromosomal DNA with one or more restriction enzymes, by amplifying a chromosomal region using PCR, and any suitable alternative amplification reaction. The digested or amplified fragment may subsequently be ligated into a vector suitable for replication and/or expression of the inserted fragment. Markers that are adjacent to an ORF associated with a phenotypic trait may be specifically hybridized to a DNA clone (e.g., a clone from a genomic DNA library), thereby identifying a clone on which the ORF (or a fragment of the ORF) is located. If a marker is more distant from the low palmitic acid content QTL gene, a fragment containing the ORF may be identified by successive rounds of screening and isolation of clones, which together comprise a contiguous sequence of DNA. This process is commonly referred to as "chromosome walking," and it may be used to produce a "contig" or "contig map."

Protocols sufficient to guide one of skill through the isolation of clones associated with linked markers are found in, for example, Sambrook et al. (ed.) *Molecular Cloning: A Laboratory Manual*, $2^{nd}$ ed., vol. 1-3, Cold Spring Harbor Laboratory Press, Cold Spring Harbor, N.Y., 1989; and Ausubel et al., Eds., *Current Protocols in Molecular Biology*, Chapter 2, Greene Publishing and Wiley-Interscience, NY, 1995.

VII. Plants Comprising Markers for Low Palmitic Acid Content

Some embodiments include methods for making a sunflower plant, and further include these sunflower plants, per se. In particular embodiments, such a method may comprise crossing a first parent sunflower plant comprising at least one marker allele that is positively correlated with low palmitic acid with a second sunflower plant at a marker linked to low palmitic acid described herein, and growing the female sunflower plant under plant growth conditions to yield sunflower plant progeny. Such sunflower plant progeny may be assayed for marker alleles linked to low palmitic acid content, and desired progeny may be selected. Such progeny plants, or seed thereof, may be subject to a variety of uses including, for example and without limitation, they may be sold commercially for sunflower production; used for food; processed to obtain a desired sunflower product (e.g., sunflower oil); and/or further utilized in subsequent rounds of breeding. Sunflower plants according to some embodiments include progeny plants that comprise at least one of the allelic forms of the markers described herein, such that further progeny are capable of inheriting the marker allele.

Some embodiments include methods for producing a sunflower plant comprising low palmitic acid content (e.g., decreased palmitic acid content). In particular embodiments, such methods may include production of such a plant by conventional plant breeding or by introducing an exogenous DNA (e.g., a transgene) into a sunflower variety or plant.

Thus, some embodiments include host cells and organisms that are transformed with nucleic acids corresponding to a low palmitic acid content QTL identified using at least one marker linked to low palmitic acid content described herein. In some examples, such nucleic acids may include chromosome intervals (e.g., genomic fragments), ORFs, and/or cDNAs that encode expression products that contribute to a low palmitic acid content phenotype.

Host cells may be genetically engineered (e.g., transduced, transfected, transformed, etc.) with a vector (e.g., a cloning vector, shuttle vector, or expression vector) that comprises an ORF linked to a marker of low palmitic acid content. Vectors include, for example and without limitation, plasmids; phagemids; *Agrobacterium*; viruses; naked polynucleotides (linear or circular); and conjugated polynucleotides. Many vectors may be introduced into bacteria, especially for the purpose of propagation and expansion.

Vectors may be introduced into plant tissues, cultured plant cells, and plant protoplasts by any of a variety of standard methods known in the art including, for example and without limitation: electroporation (From et al. (1985) *Proc. Natl. Acad. Sci. USA* 82:5824); infection by viral vectors such as cauliflower mosaic virus (CaMV) (see, e.g., U.S. Pat. No. 4,407,956); ballistic penetration by small particles comprising the nucleic acid (Klein et al. (1987) *Nature* 327:70); use of pollen as vector (PCT International Patent Publication No. WO 85/01856); and use of *Agrobacterium tumefaciens* or *A. rhizogenes* carrying a T-DNA plasmid in which DNA fragments are cloned (Fraley et al. (1983) *Proc. Natl. Acad. Sci. USA* 80:4803). Any suitable method, including without limitation the specific methods explicitly identified herein, which provides for effective introduction of a nucleic acid into a cell or protoplast, may be employed in certain embodiments of the invention.

Engineered host cells can be cultured in conventional nutrient media or media modified for, for example, activating promoters or selecting transformants. In some embodiments, host plant cells may be cultured into transgenic plants. Plant regeneration from cultured protoplasts is described in, for example, Evans et al. (1983) "Protoplast Isolation and Culture," In *Handbook of Plant Cell Cultures* 1, MacMillan Publishing Co., NY, pp. 124-176; Davey (1983) "Recent Developments in the Culture and Regeneration of Plant Protoplasts," In *Protoplasts*, Birkhauser, Basel, pp. 12-29; Dale (1983) "Protoplast Culture and Plant Regeneration of Cereals and Other Recalcitrant Crops," In *Protoplasts*, supra, pp. 31-41; and Binding (1985) "Regeneration of Plants," In *Plant Protoplasts*, CRC Press, Boca Raton, Fla., pp. 21-73. Additional resources providing useful details regarding plant cell culture and regeneration include Payne et al. (1992) *Plant Cell and Tissue Culture in Liquid Systems*, John Wiley & Sons, Inc., NY; Gamborg and Phillips (eds.) (1995) *Plant Cell, Tissue and Organ Culture; Fundamental Methods*, Springer Lab Manual, Springer-Verlag (Berlin Heidelberg N.Y.); and R. R. D. Croy (Ed.) *Plant Molecular Biology* (1993) Bios Scientific Publishers, Oxford, UK (ISBN 0 12 198370 6).

Transformed plant cells that are produced using any of the above transformation techniques may be cultured to regenerate a whole plant that possesses the transformed genotype and thus the desired phenotype. Such regeneration techniques generally rely on manipulation of certain phytohormones in a tissue culture growth medium, typically relying on a biocide and/or herbicide marker that has been introduced into the cell together with the desired nucleotide sequences. Regeneration and growth processes used to produce a whole plant generally include the steps of selection of transformant cells and shoots; rooting the transformant shoots; and growth of the plantlets in soil.

Plant transformation with nucleic acids that lower palmitic acid content (e.g., that comprise markers described herein) may be used to transform species other than sunflower. For example, it is contemplated that expression products from QTLs that contribute to or provide a low palmitic acid content phenotype in sunflower can also decrease palmitic acid content when transformed and expressed in other agronomically and horticulturally important plant species. Such species include dicots, for example and without limitation, of the families: Leguminosae (including pea, beans, lentil, peanut, yam bean, cowpeas, velvet beans, soybean, clover, alfalfa, lupine, vetch, lotus, sweet clover, wisteria, and sweetpea) and Compositae (the largest family of vascular plants, including at least 1,000 genera, including important commercial crops such as sunflower). Additional plants comprising nucleic acids that lower palmitic acid content (e.g., that comprise markers described herein) may be plants from among the genera: *Allium, Apium, Arachis, Brassica, Capsicum, Cicer, Cucumis, Curcubita, Daucus, Fagopyrum, Glycine, Helianthus, Lactuca, Lens, Lycopersicon, Medicago, Pisum, Phaseolus, Solanum, Trifolium, Vigna*, and many others. Common crop plants which may be used in particular examples include, for example and without limitation: soybean, sunflower, canola, peas, beans, lentils, peanuts, yam beans, cowpeas, velvet beans, clover, alfalfa, lupine, vetch, sweet clover, sweetpea, field pea, fava bean, broccoli, brussel sprouts, cabbage, cauliflower, kale, kohlrabi, celery, lettuce, carrot, onion, pepper, potato, eggplant and tomato.

VIII. Systems for Detecting and/or Correlating Low Palmitic Acid Content Markers Systems, including automated systems, for identifying plants that comprise at least one marker linked to a low palmitic acid phenotype in sunflower, and/or for correlating presence of a specific linked marker allele with low palmitic acid content, are also included in some embodiments. Exemplary systems may include probes useful for allele detection at a marker locus described herein; a detector for detecting labels on the probes; appropriate fluid handling elements and temperature controllers, for example, that mix probes and templates and/or amplify templates; and/or system instructions that correlate label detection to the presence of a particular marker locus or allele.

In particular embodiments, a system for identifying a sunflower plant predicted to have low palmitic acid content is provided. Such a system may include, for example and without limitation: a set of marker primers and/or probes configured to detect at least one allele of at least one marker linked to low palmitic acid content (e.g., HA0031B, HA0908, HA1665, HA0304A, HA0850, HA0743, HA0870, HA0907, HA0612A, and a marker linked to at least one of the foregoing); a detector that is configured to detect one or more signal outputs from the set of marker probes or primers, or amplicon thereof, thereby identifying the presence or absence of the allele; and system instructions that correlate the presence or absence of the allele with low (e.g., decreased) or higher palmitic acid content.

A system that performs marker detection and/or correlation may include a detector that is configured to detect one or more signal outputs from the set of marker probes or primers, or amplicon thereof. The precise configuration of the detector may depend on the type of label used to detect a marker allele. Particular examples may include light detectors and/or radioactivity detectors. For example, detection of light emission or other property of a labeled probe may be indicative of the presence or absence of a marker allele interacting with the probe (e.g., via specific hybridization). The detector(s) optionally monitors one or a plurality of signals from an amplification reaction. For example, a detector may monitor optical signals which correspond to "real time" amplification assay results.

A wide variety of signal detection devices are available including, for example and without limitation, photo multiplier tubes; spectrophotometers; CCD arrays; arrays and array scanners; scanning detectors; phototubes and photodiodes; microscope stations; galvo-scanns; and microfluidic nucleic acid amplification detection appliances. In addition to the type of label used to detect a marker allele, the precise configuration of a detector may depend, in part, on the instrumentation that is most conveniently obtained for the user. Detectors that detect fluorescence, phosphorescence, radioactivity, pH, charge, absorbance, luminescence, temperature, or magnetism may be used in some examples.

The precise form of instructions provided in a system according to some embodiments may similarly vary, depending on the components of the system. For example, instructions may be present as system software in one or more integrated unit(s) of the system, or they may be present in one or more computers or computer readable media operably coupled to a detector. In some examples, system instructions include at least one reference table that includes a correlation between the presence or absence of a particular marker allele in a plant or germplasm and a predicted palmitic acid content. Instructions may also include directions for establishing a user interface with the system; e.g., to permit a user to view results of a sample analysis and to input parameters into the system.

A system may include in particular embodiments components for storing or transmitting computer readable data representing or designating detected marker alleles, for example, in an automated (e.g., fully automated) system. For example, a computer readable media may be provided that includes cache, main, and storage memory, and/or other electronic data storage components (e.g., hard drives, floppy drives, and storage drives) for storage of computer code. Data representing alleles detected by the method of the present invention can also be electronically, optically, or magnetically transmitted in a computer data signal embodied in a transmission medium over a network, such as an intranet or internet or combinations thereof. A system may also or alternatively transmit data via wireless, infrared, or other available transmission alternatives.

During operation, the system typically comprises a sample that is to be analyzed, such as a plant tissue, or material isolated from the tissue such as genomic DNA, amplified genomic DNA, cDNA, amplified cDNA, RNA, amplified RNA, or the like.

In some embodiments, a system may be comprised of separate elements, or may alternatively be integrated into a single unit for convenient detection of markers alleles, and optionally for additionally performing marker-phenotype correlations. In particular embodiments, the system may also include a sample, for example and without limitation, genomic DNA; amplified genomic DNA; cDNA; amplified cDNA; RNA; and amplified RNA, from sunflower or from a selected sunflower plant tissue.

Automated systems provided in some embodiments optionally include components for sample manipulation;

e.g., robotic devices. For example, an automated system may include a robotic liquid control armature for transferring solutions (e.g., plant cell extracts) from a source to a destination (e.g., from a microtiter plate to an array substrate) that may be operably linked to a digital computer (e.g., in an integrated computer system). An input device for entering data to the digital computer to control high throughput liquid transfer by the robotic liquid control armature (and, optionally, to control transfer by the armature to the solid support) may also be a feature of an automated system. Many automated robotic fluid handling systems are commercially available. For example, a variety of automated systems that utilize various Zymate™ systems, and typically include, robotics and fluid handling modules, are available from Caliper Technologies Corp. (Hopkinton, Mass.). Similarly, the common ORCA® robot, which is used in a variety of laboratory systems (e.g., for microtiter tray manipulation) is also commercially available from, for example, Beckman Coulter, Inc. (Fullerton, Calif.). As an alternative to conventional robotics, microfluidic systems for performing fluid handling and detection are now widely available from Caliper Technologies and Agilent technologies (Palo Alto, Calif.).

In particular embodiments, a system for molecular marker analysis may include, for example and without limitation, a digital computer comprising high-throughput liquid control software; a digital computer comprising image analysis software for analyzing data from marker labels; a digital computer comprising data interpretation software; a robotic liquid control armature for transferring solutions from a source to a destination; an input device (e.g., a computer keyboard) for entering data into the system (e.g., to control high throughput liquid transfer by the robotic liquid control armature); and an image scanner for digitizing label signals from labeled probes.

Optical images (e.g., hybridization patterns) viewed and/or recorded by a camera or other device (e.g., a photodiode and data storage device) may be further processed in any of the embodiments herein. For example and without limitation, such images may be processed by digitizing the image and/or storing and analyzing the image on a computer. A variety of commercially available peripheral equipment and software is available for digitizing, storing and analyzing a digitized video or digitized optical image, for example, using various computer and programming platforms.

Some embodiments also include kits useful for identifying plants that comprise at least one marker linked to a low palmitic acid phenotype in sunflower, and/or for correlating presence of a specific linked marker allele with low palmitic acid content. In some examples, such a kit may include appropriate primers or probes for detecting at least one marker linked to low palmitic acid content and particular marker alleles; and instructions for using the primers or probes to detect the at least one marker and correlate the marker allele with a predicted palmitic acid content. A kit may in some examples include packaging materials for packaging probes, primers, and/or instructions; and controls (e.g., control amplification reactions that include probes, primers or template nucleic acids for amplifications, and molecular size markers).

In some embodiments, a kit or system for identifying plants that comprise at least one marker linked to a low palmitic acid phenotype in sunflower, and/or for correlating presence of a specific linked marker allele with low palmitic acid content may include nucleic acids that detect particular SSR QTL markers described herein. For example, a system or kit may comprise an amplification primer pair capable of initiating DNA polymerization by a DNA polymerase on a sunflower nucleic acid template to generate a sunflower marker amplicon, where the marker amplicon corresponds to a sunflower marker selected from HA0031B, HA0908, HA1665, HA0304A, HA0850, HA0743, HA0870, HA0907, HA0612A, and a marker linked to at least one of the foregoing. For example, the primer pair that is specific for the marker can be selected from the primer pairs set forth in Table 6, or their equivalents.

EXAMPLES

The following examples are offered to illustrate, but not to limit, certain embodiments of the invention. It is understood that the examples and embodiments described herein are for illustrative purposes only, and persons skilled in the art will recognize various reagents, techniques, systems, and parameters that can be altered without departing from the spirit or scope of the invention.

Example 1: Natural Variation for Palmitic Acid Content in Sunflower

Natural variation of palmitic acid content in sunflower was measured based upon the AOCS™ method Ce 2-66(97) (AOCS™ product code MC-CE266).

Five sunflower seeds from each sample to be tested were placed into a labeled 96-well extraction plate (Corning Inc. catalog no. 4411) containing one ⅛-inch steel ball (Small Parts Inc. catalog no. BS-0125-C). 200 µL heptanes was added to each well, which were then capped. The capped samples were placed in a GenoGrinder™ for 2.0 minutes at 1300 strokes/minute. Samples were removed, and any unground samples were crushed by hand with a spatula and re-ground.

After the first grind, 400 µL heptanes was added to each well, and the material was re-ground at 1300 strokes/minute. The samples were then centrifuged for 10 minutes at 3700 rpm at 6° C. Then, using a Beckman Coulter MC robot, the supernatant was transferred to a 96-well plate with glass inserts (MicroLiter Analytical Supplies Inc. catalog no. 07-8045 MB-1200) containing 400 µL heptanes. 40 µL 1% sodium methoxide was then added to each well. Sodium methoxide was diluted from a stock 30% solution with methanol (Sigma-Aldrich Fluka catalog no. 71748). The plates were capped with a Teflon mat cap, and incubated at room temperature for 60 minutes prior to analysis.

Samples were analyzed to determine their fatty acid compositions on an Agilent 6890 GC-FID (Agilent Technologies) equipped with a J&W Scientific DB-23 15 m×0.25 mm ID column and 0.25 µm film thickness (Agilent Technologies, catalog no. 122-2312). The initial oven temperature was 200° C., which temperature was maintained for the duration of the run. The inlet was set to split ratio of 1:50 and a temperature of 280° C. A ramped flow rate of 0.8 mL/minute helium was maintained for the initial two minutes. The flow was then increased at a rate of 1.0 mL/minute to 2.5 mL/minute, where it was held for 1.5 minutes. The detector was set to 300° C. with a constant carrier gas make up and column flow of 30 mL/minute, fuel hydrogen flow of 30 mL/minute, and oxidizer flow of 400 mL/minute. An injection volume of 2 µL it was used for all samples.

Palmitic acid methyl ester peaks were identified by comparison with the retention times of methyl ester reference standards (Nu-Chek-Prep, Inc., GLC#428). See FIG. 1 and Table 1. Individual percent areas were calculated for all analytes in the reference standard based upon the total integrated chromatographic peak areas. A heptane blank was also injected to identify any contamination on the GC.

TABLE 1

Statistics of palmitic acid content distribution

| Distribution | Quantile | % palmitic acid |
|---|---|---|
| 100.0% | maximum | 15.05 |
| 99.5 | | 5.87 |
| 97.5 | | 5.23 |
| 90.0 | | 4.63 |
| 75.0 | quartile | 4.20 |
| 50.0 | median | 3.72 |
| 25.0 | quartile | 3.21 |
| 10.0 | | 2.92 |
| 2.5 | | 2.66 |
| 0.5 | | 2.41 |
| 0.0 | minimum | 0.00 |

Figure 2:
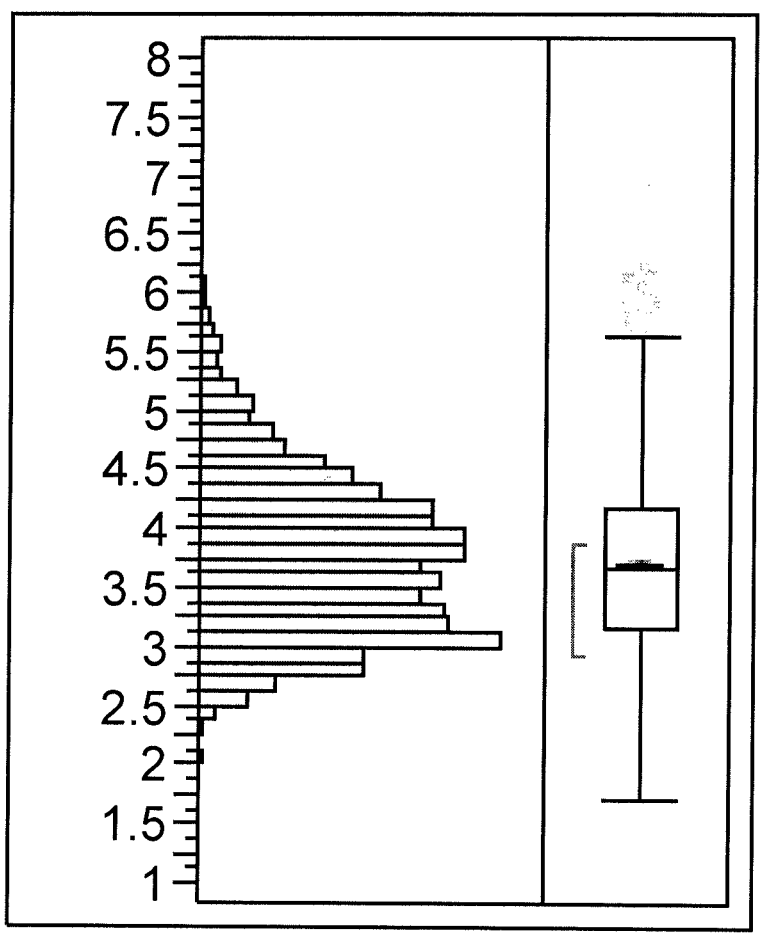
FIG. 2 includes a graphical display showing the distribution of the palmitic acid content of 23,040 samples. Values describing the distribution are set forth in Tables 1-2.

Using this method, the palmitic acid content of field grown samples was assessed on sunflower varieties that were developed as part of a seven-year sunflower breeding program. The distribution of the palmitic acid contents measured is presented in FIG. 2 and Table 2. Typically observed values for palmitic acid in conventional sunflower germplasm ranged from approximately 2.5% to 6% of total fatty acids, with a mean of 3.75%.

TABLE 2

Statistics of palmitic acid content distribution

| Mean | 3.74945 |
|---|---|
| Std. Dev. | 0.70766 |
| Std. Err. Mean | 0.00466 |
| Upper 95% Mean | 3.75858 |
| Lower 95% Mean | 3.74031 |

Example 2: Identification of Germplasm with Low Palmitic Acid Content

A low palmitic acid profile was discovered during a program designed to improve an elite black-hulled, high linoleic acid sunflower line (687R) by breeding it with a line having an elevated oleic acid profile. This was accomplished by means of backcross breeding using as the high oleic acid donor a striped-hull, high oleic acid confection parent (H280R). H280R has, in general, a lower palmitic acid content, but the observed level is not normally below about 2.5%. To achieve the targeted oleic acid levels, FAME analysis as described in Example 1 was conducted at each generation during this back-cross breeding program. During the routine screening of fatty acid levels, a segregant was observed that had substantially reduced levels of palmitic acid. In Table 3, the palmitic acid content values for four individuals from the first back-cross generation of the back-cross breeding program of 687R with H280R is shown.

TABLE 3

Palmitic acid values determined using protocol described in Example 1 of a bulked sample of 8-10 seeds from four heads selected from the first back-cross breeding generation of 687R/H280R

| Head | Palmitic acid content (%) |
|---|---|
| 1 | 2.18 |
| 2 | 2.13 |

TABLE 3-continued

Palmitic acid values determined using protocol described in Example 1 of a bulked sample of 8-10 seeds from four heads selected from the first back-cross breeding generation of 687R/H280R

| Head | Palmitic acid content (%) |
|---|---|
| 3 | 2.06 |
| 4 | 2.04 |
| H280R | 3.18 |

Example 3: Variation for Palmitic Acid Content in a Sunflower Population Made Between a Low Palmitic Acid Parent and a Conventional Sunflower Elite Parent Variation in the palmitic acid content when an elite sunflower inbred is crossed to a source of the reduced palmitic acid content was demonstrated by crossing a high oleic acid restorer (line-R) with a low palmitic acid source derived from the discovery described in Example 2. The low palmitic acid source had been converted to a cytoplasmic male sterile background (line-A). An $F_2$ population from the cross of line-A by line-R was generated, and 384 seeds were collected. The seeds were cut in half, with half of the seed being analyzed according to the protocol described in Example 1. The other half of the seed was planted for subsequent analysis. The summary statistics for the palmitic acid content in the $F_2$ population line-A/line-R (N=384) are presented in Tables 4-5.

TABLE 4

Statistics of palmitic acid content distribution in an $F_2$ population between an elite inbred having typical palmitic acid content with a line having low palmitic acid

| Distribution | Quantile | % palmitic acid |
|---|---|---|
| 100.0% | Maximum | 4.216 |
| 99.5 | | 4.216 |
| 97.5 | | 3.612 |
| 90.0 | | 3.342 |
| 75.0 | Quartile | 3.1995 |
| 50.0 | Median | 2.989 |
| 25.0 | Quartile | 2.5995 |
| 10.0 | | 1.976 |
| 2.5 | | 1.734 |
| 0.5 | | 1.648 |
| 0.0 | Minimum | 1.648 |

TABLE 5

Statistics of palmitic acid content distribution in an $F_2$ population between an elite inbred having typical palmitic acid content with a line having low palmitic acid

| Mean | 2.83964 |
|---|---|
| Std. Dev. | 0.51878 |
| Std. Err. Mean | 0.02647 |
| Upper 95% Mean | 2.89169 |
| Lower 95% Mean | 2.78759 |

Example 4: Demonstration of Bimodal Distribution of Palmitic Acid Content

Figure 3:
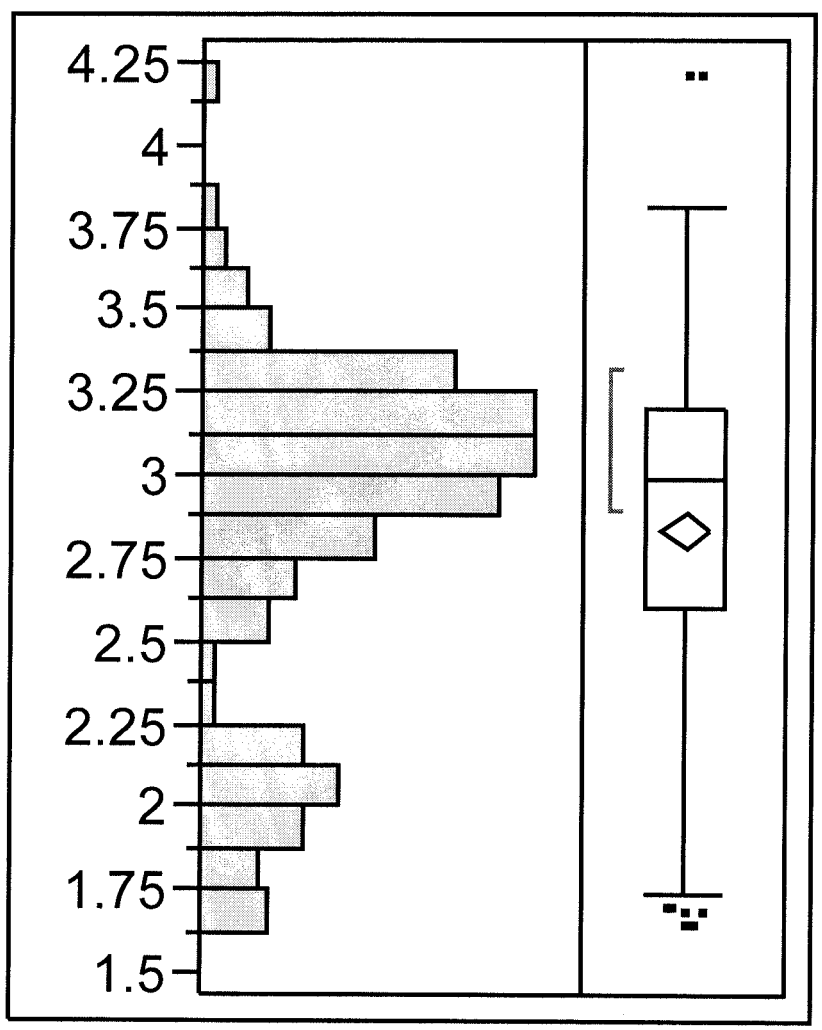
FIG. 3 includes a histogram of the palmitic acid content of an $F_2$ population of 384 individuals obtained from a cross of an elite sunflower line with a line having low palmitic acid content.

The distribution of palmitic acid content in the population described in Example 3 is presented in FIG. 3. The distribution is bimodal: part of the population is centered around about 3.15% palmitic acid, with a lower tail ending at about 2.5% and an upper tail extending to about 4%; and a second part of the population is centered at about 2.1% palmitic acid, with a lower tail reaching about 1.75% and an upper tail extending to about 2.5%. From the quantiles presented in Example 3 it was observed that 25% of the population has a palmitic acid content below 2.6%, with the remainder of the population having a higher palmitic acid content. The value of the first quartile (2.6%) corresponds closely with the inflection point where the bimodal distribution transitions from the lower cluster to the upper cluster. Noting that there is a 3:1 ratio between individuals with a higher palmitic acid content and those with a lower value, it was concluded that there is a single, major genetic element that is responsible for low palmitic acid content in this population, with the recessive allele conferring the low palmitic acid phenotype.

Example 5: QTL Mapping of a Genetic Determinant of Palmitic Acid Content

A major locus for palmitic acid content was mapped on to sunflower linkage group 5 (LG5) using microsatellite or SSR markers and the palmitic acid content data presented in Examples 3 and 4.

The maps in sunflower are usually referred to by linkage group. Maps of linkage group 5 are available. See Yu et al. (2003) *Crop Sci.* 43:367-87; see also Tang et al. (2002) *Theor. Appl. Genet.* 105:1124-36. It should be noted that sunflower linkage group numbers of maps developed by European scientists are different from, for example, the ones set forth in the above-cited references. The chromosome numbers corresponding to linkage groups in sunflower have not yet been defined.

TABLE 6

Primer sequences and map locations of SSR markers mapped on LG5 for identifying the palmitic acid locus

| Marker | Map Position (cm) | Forward Primer Sequence | Reverse Primer Sequence |
|---|---|---|---|
| HA0357_H757B | 0.0 | GTTCCTGTCGGGTAACTGTAGC (SEQ ID NO: 1) | CATTGATGGAGATGGCTGG (SEQ ID NO: 2) |
| HA0694B_H280R | 17.8 | GCCGTGAATAATGGGATTGA (SEQ ID NO: 3) | GATTGGGTCAGCTTGTGTGA (SEQ ID NO: 4) |
| HA1485 | 19.7 | GGGAAGTGGGCTTGTCTATGTAT (SEQ ID NO: 5) | AACACACCGAAATCACCTATGAA (SEQ ID NO: 6) |
| HA1838 | 20.1 | AGAGGAATGAGATCGGGTTGAT (SEQ ID NO: 7) | GTGGGACAACTCAGCAACGTC (SEQ ID NO: 8) |
| HA1489_H280R | 20.5 | CTTATTCCAAGGACGCATAGTCG (SEQ ID NO: 9) | CGATGGTATGATTCTCGACGTTA (SEQ ID NO: 10) |
| HA1146B | 21.6 | ACACCAACCAGACGCAGAAT (SEQ ID NO: 11) | GTGCAAGAACGAGGAAGAGG (SEQ ID NO: 12) |
| HA0037 | 21.8 | GAACATGGCCATAACTCATAGACG (SEQ ID NO: 13) | CCTTCGACCCAACATC (SEQ ID NO: 14) |
| HA0654 | 21.8 | ACGCACATGAGAGAGAAAGAG (SEQ ID NO: 15) | ACCTTCGACCCAACATCAAG (SEQ ID NO: 16) |
| HA1620_H280R | 22.6 | TTTCGTGATGGTGATTGATGATT (SEQ ID NO: 17) | CAGCAACTCTGACCGTTTCATTA (SEQ ID NO: 18) |
| HA0031B | 23.0 | CTCACGAAACTCTTCATGCTG (SEQ ID NO: 19) | CTCTCACACTTACTGAAC (SEQ ID NO: 20) |
| HA0908 | 23.1 | TTGTCTTCATCTGCGTGTGA (SEQ ID NO: 21) | TTGCTGTTGTTGATCGGTGT (SEQ ID NO: 22) |
| HA1665 | 23.2 | CCTAAGGGGATGAATTCTCTTTC (SEQ ID NO: 23) | AACTTCCAATGTTCTCCAACCAT (SEQ ID NO: 24) |
| HA0304A_H757B | 23.6 | GTGCCCTAACACTGTTCCGT (SEQ ID NO: 25) | AGCGAAAGGATCGAGAATC (SEQ ID NO: 26) |
| HA0850_H757B | 23.8 | CCCTGGAGTGTATGTCCGTTA (SEQ ID NO: 27) | ATCCGTCTGCTGCCTAATCC (SEQ ID NO: 28) |
| HA0743_H757B | 24.2 | ACGGAAAGCTCTTGAAAGCA (SEQ ID NO: 29) | GCGGGCATTCCAACTAGTAA (SEQ ID NO: 30) |
| HA0870 | 24.3 | GTGCGTTGGCTCTTATGGAT (SEQ ID NO: 31) | AGTGATGGCATTCCCAATTT (SEQ ID NO: 32) |
| HA0907 | 24.6 | CATGAACATCGCCAATTCAG (SEQ ID NO: 33) | TGCAAGGAACCATCAGAATC (SEQ ID NO: 34) |

TABLE 6-continued

Primer sequences and map locations of SSR markers mapped on LG5 for identifying the palmitic acid locus

| Marker | Map Position (cm) | Forward Primer Sequence | Reverse Primer Sequence |
|---|---|---|---|
| HA0612A_H757B | 25.8 | CTTGGGTTCTTCATAACTC (SEQ ID NO: 35) | CATGTAATCACCTTTCAAG (SEQ ID NO: 36) |
| HA1923 | 27.1 | AACCAAAGATTCAAGGCAATCA (SEQ ID NO: 37) | CAGACATTAGACGCGAAGCAG (SEQ ID NO: 38) |
| HA1357A | 28.2 | CACAAAACAATCGCTAAAAGAACA (SEQ ID NO: 39) | AATGATGATGGTCACGAAGAAGA (SEQ ID NO: 40) |
| HA1357B_H757B | 29.5 | CACAAAACAATCGCTAAAAGAACA (SEQ ID NO: 39) | AATGATGATGGTCACGAAGAAGA (SEQ ID NO: 40) |
| HA1819_H280R | 30.9 | GTTTCGGGTGGGGATTACGG (SEQ ID NO: 41) | ATGGTCGACAACAAGCGCAAAC (SEQ ID NO: 42) |
| HA0894 | 33.2 | TGGTGGAGGTCACTATTGGA (SEQ ID NO: 43) | AGGAAAGAAGGAAGCCGAGA (SEQ ID NO: 44) |
| HA1790 | 37.6 | TCCCCAAACTTGCGTGTAGGT (SEQ ID NO: 45) | CATTACAAACCACAGCTCCTTCC (SEQ ID NO: 46) |
| HA0041 | 47.1 | CTAGCAACCAACCTCATTG (SEQ ID NO: 47) | GTCTCCTTCTCTTTCTCGGC (SEQ ID NO: 48) |
| HA1313 | 52.3 | CGACCCACCTAGTAAAAGCAAAC (SEQ ID NO: 49) | TGCCATAAAAAGATTTGGTCTCC (SEQ ID NO: 50) |
| HA1776_H757B | 59.6 | TCACAGGAGAATGCAAAGAGTG (SEQ ID NO: 51) | GCATAATAGGAGTAACTGCCAAAAC (SEQ ID NO: 52) |

PCR Procedures for SSR Markers.

PCR reactions were performed in a GeneAmp™ PCR System 9700 (Applied Biosystems) with a dual-384 well block. Each PCR reaction was carried out in a volume of 8 µL containing 10 ng of genomic DNA with a final concentration of 1× Qiagen™ PCR buffer (Qiagen, Valencia, Calif.), 0.25 µM of each primer (forward and reverse), 1 mM $MgCl_2$, 0.1 mM of each dNTP, 0.4% PVP, and 0.04 units of HotStart™ Taq DNA polymerase (Qiagen, Valencia, Calif.).

PCR conditions were set up as follows: 12 minutes at 95° C. for template DNA denaturing; 40 cycles for DNA amplifications (each cycle: 5 seconds at 94° C. for denaturing, 15 seconds at 55° C. for annealing, and 30 seconds at 72° C. for extension); and 30 minutes at 72° C. for final extensions.

Fragment Analysis.

PCR products of different primer pairs were multiplexed in a final volume of 100 µL (using autoclaved water to bring the volume to 100 µL). 0.5 µL multiplexed PCR products were mixed with 5 µL of loading buffer. Gels were run on an AB3730XL DNA Analyzer (Applied Biosystems) with G5-RCT spectral matrix using standard conditions. Data were then imported into GeneMapper® version 4.0 (Applied Biosystems). All dye colors were imported, and the 2 highest peaks, with minimum intensity of 100 relative fluorescent units (rfu), were labeled. Alleles were assigned a numeric value according to PCR fragment size. Numeric allele scores were imported into Excel™ (Microsoft), where they were converted into formats appropriate for JoinMap™ 3.0 and MapQTL™ 4.0.

Statistical Analysis

Linkage Mapping.

Join Map™ 3.0 was used to create a genetic linkage map of the line-Mine-R $F_2$ population. JoinMap™ 3.0 requires one input file, referred to as a locus genotype file. In the locus genotype file, elite parent alleles were called as "A," donor parent alleles were called as "B," while heterozygous alleles were called as "H." Missing data were represented with a dash in the locus genotype file. Results were calculated in Kosambi centimorgans. The map generated from this analysis was compared to the public map (see S. Tang, J. K. Yu, M. B. Slabaugh, D. K. Shintani, S. J. Knapp (2002) Simple sequence repeat map of the sunflower genome. *Theor. Appl. Genet.* 105:1124-1136) for final data interpretation.

QTL Analysis.

Interval mapping for palmitic acid content was conducted using MapQTL™ 4.0 to locate a potential QTL. MapQTL™ 4.0 requires three input files, including a locus genotype file, a map file, and a quantitative data file. The locus genotype file contained the genotype codes for all loci of the segregating population as described above. The map file, generated from JoinMap™ 3.0, contained the estimated map positions on LG5 of the 27 loci listed in Example 5. The quantitative data file contained the palmitic acid content as determined using the analytical chemistry methods described in Example 1.

Interval mapping analysis evaluates the likelihood of a QTL located along an interval between two markers. Jansen (1993) *Genetics* 135:205-11. Interval mapping analysis was performed, and the likelihood that a QTL was within an interval was calculated. When a LOD score exceeded the predefined significance threshold of P<0.05 or P<0.01, as calculated from a 1,000 iteration experiment-wise permutation test (Churchill and Doerge (1994) *Genetics* 138(3):963-71), a QTL determination was made. The position with the largest LOD on the linkage group was used as the estimated position of the QTL on the map. As this was an $F_2$ population, it was possible to perform interval mapping using a statistical model to detect a QTL associated with additive genetic variance alone, and using a statistical model that accounted for (and therefore detected) a QTL associated with both additive and dominant genetic variation. The previously defined data were analyzed using both models.

Example 6: Selecting Backcross Progeny According to Palmitic Acid Content

The markers described herein were used to select progeny obtained by means of backcross breeding using a donor line having the allele associated with the low palmitic acid phenotype. An elite line with a palmitic acid content of approximately 3.5% was crossed to a donor line having the alleles associated with the low palmitic acid phenotype at loci HA0907, HA0041, HA1790, HA1665, HA0908, and HA1620. A selection from the resulting progeny was backcrossed to the elite line to produce the first backcross generation. A selection from the first backcross generation was backcrossed again to the elite line to produce the second backcross generation. The genotype of an individual from the second backcross generation is shown in Table 7.

TABLE 7

Genotypes of an elite line having an elevated palmitic acid phenotype, a donor with the alleles associated with the reduced palmitic acid phenotype, and a selection from the second backcross generation with these two lines as the recurrent parent and donor, respectively.

| | | Chromosome 5 | | | | | | |
|---|---|---|---|---|---|---|---|---|
| Sample | | HA0907 18 | HA0041 20 | HA1790 25 | HA1665 31 | HA0908 35 | HA1620 39 | End 59 |
| ON6725R | | A, A | A, A | A, A | A, A | A, A | A, A | |
| NS1982.8 | | B, B | B, B | B, B | B, B | B, B | B, B | |
| ON6725R[2]/NS1982.8#1=1=3 | Plant #19 | A, A | A, B | A, B | A, B | A, B | A, B | |

Since the low palmitic acid content phenotype is recessive, the individual from the second backcross generation shown in Table 7 would not display the low palmitic acid phenotype itself. To verify that the alleles associated with reduced palmitic acid will confer the low palmitic acid phenotype in the elite background, a progeny test was performed. The individual in Table 7 was self-pollinated, and eight seeds representing the progeny of the self pollination were subjected to FAME analysis to determine the palmitic acid content. The results, presented in Table 8, show that three of the eight progeny have the low palmitic acid content phenotype, consistent with the expected ratio of one to three for a recessive trait controlled by a single locus. This result demonstrates that the low palmitic acid content phenotype is being inherited in progeny.

TABLE 8

Palmitic acid phenotypes of eight individuals from the self pollination of plant number 19 from the second backcross generation of ON6725R[2]/NS1982.8#1=1=3

| Individual | Palmitic acid content (%) |
|---|---|
| 1 | 2.68 |
| 2 | 2.73 |
| 3 | 1.71 |
| 4 | 2.23 |

TABLE 8-continued

Palmitic acid phenotypes of eight individuals from the self pollination of plant number 19 from the second backcross generation of ON6725R[2]/NS1982.8#1=1=3

| Individual | Palmitic acid content (%) |
|---|---|
| 5 | 1.98 |
| 6 | 2.85 |
| 7 | 3.31 |
| 8 | 1.92 |

Example 7: Selecting Cytoplasmic Male-Sterile Maintainer Line Progeny with Elevated Palmitic Acid Content In commercial sunflower hybrid seed production, a cytoplasmic male sterility system is used to produce the required quantities of seed. The sunflower line in Example 6 was a restorer line which restores normal fertility when used as a pollinator with a female having a male sterile cytoplasm. Hybrids having the low palmitic acid content phenotype may be produced from male and female inbreds carrying the low palmitic acid QTL allele(s) linked to the markers described herein, since the low palmitic acid content phenotype is recessive. In a cytoplasmic male sterile hybrid production system, the female inbred consists of two near-isogenic lines: the A-line that carries the cytoplasm conferring male sterility; and the B-line that has a normal cytoplasm, but does not carry the restorer gene. The B-line is male fertile, and it can be used to pollinate the A-line, with the resulting progeny being male sterile, since they inherit the cytoplasm from the female A-line. These progeny are also essentially identical to the A-line parent, since the A and B lines are near-isogenic. The B-line is thus known as the maintainer line. The A-line is derived from the B-line using a cytoplasmic male sterile line as the donor and the B-line as the recurrent parent. Following repeated back-crossing with the B-line as the recurrent (male) parent, the B-line genotype can be recovered while retaining the male sterile cytoplasm of the donor. The resulting line is known as the A-line. The first step in creating a new A-line, B-line pair is to create a new B-line. The A-line is then derived from the B-line.

To demonstrate the utility of the markers described herein for the purpose of creating cytoplasmic male sterile maintainer lines having a low palmitic acid content phenotype, an elite B-line with a palmitic acid content of approximately 3.5% was crossed to a donor line having the alleles associated with the low palmitic acid phenotype at loci HA0850, HA0907, and HA0908. The remaining loci were monomorphic between the donor and recurrent parent. A selection from the resulting progeny was backcrossed to the elite line to produce a first backcross generation. The genotype of an individual from the first backcross generation is shown in Table 9.

TABLE 9

Genotypes of an elite B line having an elevated palmitic acid phenotype, a donor with the alleles associated with the reduced palmitic acid phenotype, and a selection from the first backcross generation with these two lines as the recurrent parent and donor, respectively.

| | Chromosome 5 | | | |
|---|---|---|---|---|
| Sample | HA0850 13 | HA0907 18 | HA0908 35 | End 59 |
| ON1919B | A, A | A, A | A, A | |
| NS1982.8 | B, B | B, B | B, B | |
| ON1919B[1]//CN1919B/ NS1982.8#3=1-17=5 Plant # 11 | A, A | A, B | A, B | |

To verify that the low palmitic acid alleles carried by the individual in Table 9 will confer the low palmitic acid phenotype when in the homozygous state, a progeny test was performed. The individual in Table 9 was self-pollinated, and eight seeds representing the progeny of the self-pollination were subjected to FAME analysis to determine the palmitic acid content. The results, presented in Table 10, show that two of the eight progeny had the low palmitic acid content phenotype, which is consistent with the expected ratio of one-to-three for a recessive trait controlled by a single locus. This result demonstrates that the low palmitic acid content phenotype can be introgressed into a B-line using backcross breeding.

TABLE 10

Palmitic acid phenotypes of eight individuals from the self pollination of plant number 11 from the first backcross generation of ON1919B[1]//CN1919B/NS1982.8#3=1-17=5.

| Individual | Palmitic acid content (%) |
|---|---|
| 1 | 2.74 |
| 2 | 3.16 |
| 3 | 3.01 |
| 4 | 1.77 |
| 5 | 2.97 |
| 6 | 3.47 |
| 7 | 2.73 |
| 8 | 1.87 |

Example 8: Development of Finished Cytoplasmic Male-Sterile Elite Maintainer and Restorer Lines with Elevated Palmitic Acid Content Following two generations of backcrossing, selected individuals were self-pollinated for 3 generations, and selections with desirable agronomic traits were subjected to FAME analysis. The results, shown in Table 11, demonstrate that finished elite B-lines with the low palmitic acid content phenotype can be developed using the backcross breeding method.

TABLE 11

Palmitic acid content of elite B-lines developed using the backcross breeding method

| Name | Palmitic acid content (%) |
|---|---|
| H251B[3]/NS1982.12-20=1=4-1-20-07 | 1.93 |
| ON7479B[2]/NS1982-8#2=1=5-12-10-01 | 1.96 |

Following two generations of backcrossing, selected individuals were self-pollinated for 3 generations and selections desirable agronomic traits was subjected to FAME analysis. The results, shown in Table 12, demonstrate that finished elite restorer lines with the low palmitic acid phenotype can be developed using the backcross breeding method.

TABLE 12

Palmitic acid content of elite restorer lines developed using the backcross breeding method

| Name | Palmitic acid content (%) |
|---|---|
| OND163R[4]/NS1982-16=20=2=3=13-7-2-2 | 1.79 |
| ON7385R[3]/NS1982.8=7=2=5-4-2-01 | 1.79 |

While the foregoing embodiments have been described in detail for purposes of clarity and understanding, it will be clear to one skilled in the art from a reading of this disclosure that various changes in form and detail can be made without departing from the true scope of the invention. For example, all the techniques and apparatus described above can be used in various combinations.

All publications, patents, patent applications, and/or other documents cited in this application are incorporated by reference in their entirety for all purposes to the same extent as if each individual publication, patent, patent application, and/or other document were individually indicated to be incorporated by reference for all purposes.

What may be claimed is:

1. A method for identifying and producing a sunflower plant or germplasm that comprises low palmitic acid content, the method comprising:

isolating a nucleic acid from a first sunflower plant or germplasm;

detecting whether a marker allele that positively correlates with low palmitic acid content is present in the isolated nucleic acid by amplifying the isolated nucleic acid with an amplification primer or primer pair that is complementary or partially complementary to at least a portion of the marker selected from the group consisting of HA0743_H757B and HA0612A_H757B, to generate at least one amplicon; and detecting the at least one marker amplicon;

identifying that the first sunflower plant or germplasm comprises low palmitic acid content when the at least one marker amplicon is detected; and crossing the first sunflower plant or germplasm identified for low palmitic acid content with a second sunflower plant or germplasm, to produce a sunflower plant or germplasm progeny comprising low palmitic acid content.

2. The method according to claim 1, wherein the isolated nucleic acid is a DNA molecule or RNA molecule.

3. The method according to claim 1, wherein the amplifying comprises utilizing a polymerase chain reaction (PCR) or ligase chain reaction (LCR) using the nucleic acid isolated from the first sunflower plant or germplasm as a template in the PCR or LCR.

4. The method according to claim 1, wherein detecting the at least one marker amplicon comprises using software selected from TASSEL™, GeneFlow™, and MapManager-QTX™.

5. The method according to claim 1, wherein the method comprises selecting the first sunflower plant or germplasm.

6. The method according to claim 1, wherein the method comprises selecting the sunflower plant or germplasm progeny.

7. The method according to claim 1, wherein the second sunflower plant or germplasm is a plant or germplasm from an elite sunflower variety or an exotic sunflower variety.

8. A method for identifying and producing a sunflower plant or germplasm that comprises low palmitic acid content, the method comprising:

amplifying from genomic DNA of the sunflower plant or germplasm at least one marker linked to low palmitic acid content, wherein the at least one marker is selected from the group consisting of HA0743_H757B and HA0612A_H757B, to yield a marker amplicon, wherein the amplifying comprises:

admixing an amplification primer or amplification primer pair with a nucleic acid isolated from the sunflower plant or germplasm, wherein the primer or primer pair is complementary or partially complementary to at least a portion of the marker, and is capable of initiating DNA polymerization by a DNA polymerase using the sunflower nucleic acid as a template, and extending the primer or primer pair in a DNA polymerization reaction comprising a DNA polymerase and a template nucleic acid to generate at least one amplicon;

detecting the at least one marker amplicon; and crossing the sunflower plant or germplasm with a different sunflower plant or germplasm.

9. The method according to claim 8, wherein the different sunflower plant or germplasm is a plant or germplasm from an elite sunflower variety or an exotic sunflower variety.

* * * * *